US009907705B2

(12) United States Patent
Harris et al.

(10) Patent No.: US 9,907,705 B2
(45) Date of Patent: Mar. 6, 2018

(54) DISPENSING APPARATUS FOR APPLYING ADHESIVE ON AN ELASTIC STRAND IN ASSEMBLY OF A PERSONAL DISPOSABLE HYGIENE PRODUCT

(71) Applicant: Nordson Corporation, Westlake, OH (US)

(72) Inventors: Michael W. Harris, Eau Claire, WI (US); Joel E. Saine, Dahlonega, GA (US)

(73) Assignee: Nordson Corporation, Westlake, OH (US)

( * ) Notice: Subject to any disclaimer, the term of this patent is extended or adjusted under 35 U.S.C. 154(b) by 0 days.

(21) Appl. No.: 14/644,318

(22) Filed: Mar. 11, 2015

(65) Prior Publication Data

US 2015/0182983 A1 Jul. 2, 2015

Related U.S. Application Data

(63) Continuation of application No. 14/456,418, filed on Aug. 11, 2014, now Pat. No. 9,067,394, which is a (Continued)

(51) Int. Cl.
*B05C 5/02* (2006.01)
*A61F 13/15* (2006.01)
(Continued)

(52) U.S. Cl.
CPC .. *A61F 13/15593* (2013.01); *A61F 13/49017* (2013.01); *B05C 5/0241* (2013.01);
(Continued)

(58) Field of Classification Search
CPC .................................................. B05C 5/0241
See application file for complete search history.

(56) References Cited

U.S. PATENT DOCUMENTS 2,428,284 A 9/1947 Krogel
2,823,518 A 2/1958 Murray
(Continued)

FOREIGN PATENT DOCUMENTS

CN 101849872 A 10/2010
EP 0096453 A2 12/1983
(Continued)

OTHER PUBLICATIONS

Nordson Corporation, Using Foamed Materials for Bonding and Sealing, Brochure, 2005.
(Continued)

*Primary Examiner* — Xiao S Zhao
(74) *Attorney, Agent, or Firm* — Baker & Hostetler LLP

(57) ABSTRACT

A method of dispensing adhesive onto a stretched elastic strand includes applying a first volume of adhesive onto a first portion of the elastic strand, applying a second volume of adhesive onto a second portion of the elastic strand, and applying a third volume of adhesive onto a third portion of the elastic strand. The second volume is less than the first and third volumes. When the elastic strand is adhesively secured to a substrate to form a personal disposable hygiene product, the first and third portions of the elastic strand define opposing ends of the elastic strand, which are adhered with a larger amount of adhesive capable of limiting movement of the strand at the opposing ends, thereby maintaining the integrity of the bond between the substrate and the elastic strand.

13 Claims, 9 Drawing Sheets

Related U.S. Application Data continuation-in-part of application No. 13/444,126, filed on Apr. 11, 2012, now Pat. No. 9,034,425.

(51) Int. Cl.
  *A61F 13/49* (2006.01)
  *B05D 1/42* (2006.01)
  *B32B 37/12* (2006.01)
  *B05C 9/06* (2006.01)

(52) U.S. Cl.
  CPC .............. *B05C 9/06* (2013.01); *B05D 1/42* (2013.01); *B32B 37/1292* (2013.01)

(56) References Cited

U.S. PATENT DOCUMENTS

| | | | |
|---|---|---|---|
| 3,219,276 A | 11/1965 | Norris | |
| 3,640,461 A | 2/1972 | Koll | |
| 3,890,926 A | 6/1975 | Teed | |
| 3,911,173 A | 10/1975 | Sprague, Jr. | |
| 4,050,410 A | 9/1977 | Stroszynski | |
| 4,325,372 A | 4/1982 | Teed | |
| 4,488,665 A | 12/1984 | Cocks et al. | |
| 4,530,862 A | 7/1985 | Kerzel | |
| 4,666,542 A | 5/1987 | De Jonckheere | |
| 4,687,477 A | 8/1987 | Suzuki et al. | |
| 4,711,683 A | 12/1987 | Merkatoris | |
| 4,762,582 A | 8/1988 | de Jonckheere | |
| 4,764,234 A | 8/1988 | Smits et al. | |
| 4,785,996 A | 11/1988 | Ziecker et al. | |
| 4,815,660 A | 3/1989 | Boger | |
| 4,842,666 A | 6/1989 | Werenicz | |
| 4,891,249 A | 1/1990 | McIntyre | |
| 4,917,696 A | 4/1990 | De Jonckheere | |
| 4,949,668 A | 8/1990 | Heindel et al. | |
| 4,995,333 A | 2/1991 | Keller et al. | |
| 5,030,484 A | 7/1991 | Chino et al. | |
| 5,066,428 A | 11/1991 | Manlowe et al. | |
| 5,275,676 A | 1/1994 | Rooyakkers et al. | |
| 5,322,729 A | 6/1994 | Heeter et al. | |
| 5,338,569 A | 8/1994 | Hatch | |
| 5,340,648 A | 8/1994 | Rollins et al. | |
| 5,342,647 A | 8/1994 | Heindel et al. | |
| 5,360,629 A | 11/1994 | Milbourn et al. | |
| 5,382,312 A | 1/1995 | Raterman | |
| 5,413,654 A | 5/1995 | Igaue et al. | |
| 5,418,009 A | 5/1995 | Raterman et al. | |
| 5,421,941 A | 6/1995 | Allen et al. | |
| 5,429,694 A | 7/1995 | Herrmann | |
| 5,501,756 A | 3/1996 | Rollins et al. | |
| 5,505,995 A | 4/1996 | Leonard | |
| 5,507,909 A | 4/1996 | Rollins et al. | |
| 5,525,175 A | 6/1996 | Blenke et al. | |
| 5,540,804 A | 7/1996 | Raterman | |
| 5,576,091 A | 11/1996 | Zajaczkowski et al. | |
| 5,582,668 A | 12/1996 | Kling | |
| 5,683,752 A | 11/1997 | Popp et al. | |
| 5,688,555 A | 11/1997 | Teng | |
| 5,749,971 A | 5/1998 | Ni | |
| 5,779,799 A | 7/1998 | Davis | |
| 5,866,210 A | 2/1999 | Rosynsky et al. | |
| 5,916,393 A | 6/1999 | Shaffer et al. | |
| 5,939,136 A | 8/1999 | Cronk et al. | |
| 6,033,513 A | 3/2000 | Nakamura | |
| 6,033,723 A | 3/2000 | Kistler et al. | |
| 6,077,373 A | 6/2000 | Fletcher et al. | |
| 6,077,375 A | 6/2000 | Kwok | |
| D433,692 S | 11/2000 | Fort et al. | |
| 6,235,137 B1 | 5/2001 | Van Eperen et al. | |
| 6,248,097 B1 | 6/2001 | Beitz et al. | |
| 6,289,841 B1 | 9/2001 | Caldwell | |
| 6,291,016 B1 | 9/2001 | Donges et al. | |
| 6,296,463 B1 | 10/2001 | Allen | |
| 6,361,634 B1 | 3/2002 | White et al. | |
| 6,378,784 B1 | 4/2002 | Allen et al. | |
| 6,383,568 B1 | 5/2002 | Gast-Bray | |
| 6,422,428 B1 | 7/2002 | Allen et al. | |
| 6,436,216 B1 | 8/2002 | Grover | |
| 6,509,089 B1 | 1/2003 | Rollins et al. | |
| 6,537,373 B1 | 3/2003 | Kitano et al. | |
| 6,579,382 B2 | 6/2003 | Ito | |
| 6,589,601 B1 | 7/2003 | Shimada | |
| 6,652,693 B2 | 11/2003 | Burriss et al. | |
| 6,676,038 B2 | 1/2004 | Gressett, Jr. et al. | |
| 6,719,846 B2 | 4/2004 | Nakamura et al. | |
| 6,745,948 B1 | 6/2004 | Hidaka et al. | |
| 6,814,555 B2 | 11/2004 | Allen | |
| 6,840,404 B1* | 1/2005 | Schultz | B01F 15/0466 222/137 |
| 6,855,373 B2 | 2/2005 | Karlsson | |
| 6,863,225 B2 | 3/2005 | Nakamura | |
| 6,905,081 B2 | 6/2005 | Saidman et al. | |
| 6,911,232 B2 | 6/2005 | Crane et al. | |
| 6,926,772 B2 | 8/2005 | Leonard | |
| 6,932,802 B2 | 8/2005 | Luizzi, Jr. et al. | |
| 6,936,125 B2 | 8/2005 | Harris | |
| 7,014,911 B2 | 3/2006 | Harris | |
| D519,536 S | 4/2006 | de Leeuw et al. | |
| D521,035 S | 5/2006 | de Leeuw et al. | |
| 1,529,321 A1 | 10/2006 | Gould et al. | |
| 7,152,815 B2 | 12/2006 | Harris et al. | |
| D536,354 S | 2/2007 | Kufner et al. | |
| 7,175,108 B2 | 2/2007 | Saine | |
| D550,261 S | 9/2007 | Bondeson et al. | |
| 7,320,814 B2 | 1/2008 | Blincoe et al. | |
| 7,374,792 B2 | 5/2008 | Rosynsky et al. | |
| 7,438,763 B2 | 10/2008 | Kanke | |
| 7,462,240 B2 | 12/2008 | Harris et al. | |
| 7,465,367 B2 | 12/2008 | Day | |
| D588,617 S | 3/2009 | Burmester et al. | |
| 7,521,087 B2 | 4/2009 | Rosynsky et al. | |
| 7,541,068 B2 | 6/2009 | Tisone | |
| 7,559,487 B2 | 7/2009 | Gressett, Jr. et al. | |
| 7,578,882 B2 | 8/2009 | Harris et al. | |
| D599,388 S | 9/2009 | Schreck | |
| 7,647,885 B2 | 1/2010 | Crane et al. | |
| 7,703,705 B2 | 4/2010 | Ganzer | |
| 7,709,061 B2 | 5/2010 | Craamer et al. | |
| 7,754,040 B2 | 7/2010 | Norrby | |
| 7,798,434 B2 | 9/2010 | Bondeson et al. | |
| 7,820,001 B2 | 10/2010 | Thomas et al. | |
| 7,833,369 B2 | 11/2010 | Zhou et al. | |
| 7,846,281 B2 | 12/2010 | Muvundamina | |
| D641,767 S | 7/2011 | Juergens | |
| D643,054 S | 8/2011 | Sennrich | |
| 8,186,296 B2 | 5/2012 | Brown et al. | |
| 8,445,061 B2 | 5/2013 | McGuffey | |
| 9,409,199 B2 | 8/2016 | Nakano | |
| 2001/0000611 A1 | 5/2001 | Cline et al. | |
| 2001/0017102 A1 | 8/2001 | Caldwell | |
| 2001/0028920 A1 | 10/2001 | Ito et al. | |
| 2001/0030014 A1 | 10/2001 | Kwok | |
| 2001/0049516 A1 | 12/2001 | Shimada et al. | |
| 2001/0053420 A1 | 12/2001 | Donges et al. | |
| 2001/0054477 A1 | 12/2001 | Kwok | |
| 2002/0036050 A1 | 3/2002 | Kwok | |
| 2002/0138064 A1 | 9/2002 | Datta et al. | |
| 2003/0089447 A1 | 5/2003 | Molee et al. | |
| 2003/0104130 A1 | 6/2003 | Karlsson | |
| 2003/0161955 A1 | 8/2003 | Brumwell | |
| 2003/0161964 A1 | 8/2003 | Leonard | |
| 2003/0173018 A1 | 9/2003 | Harris | |
| 2003/0173024 A1 | 9/2003 | Hayder et al. | |
| 2003/0224105 A1 | 12/2003 | Chondroudis et al. | |
| 2004/0144494 A1 | 7/2004 | Harris et al. | |
| 2004/0158217 A1 | 8/2004 | Wu et al. | |
| 2004/0159672 A1 | 8/2004 | Auber et al. | |
| 2004/0163771 A1* | 8/2004 | Herring, Jr. | B21D 39/021 156/575 |
| 2005/0013975 A1 | 1/2005 | Brock et al. | |
| 2005/0015050 A1 | 1/2005 | Mowery et al. | |
| 2005/0137549 A1 | 6/2005 | Lindsay et al. | |
| 2005/0271806 A1* | 12/2005 | Ganzer | B05C 5/0212 427/207.1 |

(56) References Cited

U.S. PATENT DOCUMENTS

| | | |
|---|---|---|
| 2006/0251806 A1 | 11/2006 | Brock et al. |
| 2006/0254698 A1 | 11/2006 | Tachibana et al. |
| 2006/0258249 A1 | 11/2006 | Fairbanks et al. |
| 2007/0131335 A1 | 6/2007 | Zhou et al. |
| 2007/0135008 A1 | 6/2007 | Hall et al. |
| 2008/0145530 A1 | 6/2008 | Bondeson et al. |
| 2008/0245298 A1 | 10/2008 | Ayers |
| 2008/0302299 A1 | 12/2008 | Lessley et al. |
| 2009/0062761 A1 | 3/2009 | Goerg-Wood et al. |
| 2009/0206506 A1 | 8/2009 | Crane et al. |
| 2010/0024987 A1 | 2/2010 | Saine et al. |
| 2010/0221435 A1 | 9/2010 | Fork et al. |
| 2010/0221449 A1 | 9/2010 | Schlatterbeck et al. |
| 2010/0224121 A1 | 9/2010 | Klingel |
| 2010/0262101 A1 | 10/2010 | Minato et al. |
| 2010/0279127 A1 | 11/2010 | Ukai et al. |
| 2010/0297353 A1 | 11/2010 | Sahoda et al. |
| 2010/0327074 A1 | 12/2010 | Bondeson et al. |
| 2011/0012752 A1 | 1/2011 | Ferrar |
| 2011/0014369 A1 | 1/2011 | McGuffey |
| 2011/0014430 A1 | 1/2011 | McGuffey |
| 2011/0114266 A1 | 5/2011 | Petersen et al. |
| 2011/0139066 A1 | 6/2011 | Chuang et al. |
| 2012/0258246 A1 | 10/2012 | Saine et al. |

FOREIGN PATENT DOCUMENTS

| | | |
|---|---|---|
| EP | 0112638 A2 | 7/1984 |
| EP | 0380781 | 8/1990 |
| EP | 0411287 A1 | 2/1991 |
| EP | 1880772 A1 | 1/2008 |
| EP | 2679313 A2 | 1/2014 |
| EP | 2777665 A1 | 9/2014 |
| GB | 1444073 | 7/1976 |
| GB | 1455469 A | 11/1976 |
| JP | 0780377 A | 3/1995 |
| JP | 2003164786 A | 6/2003 |
| JP | 2004352494 A | 12/2004 |
| JP | 3699331 | 9/2005 |
| JP | 200982439 A | 4/2009 |
| JP | 4638674 B2 | 2/2011 |
| WO | 1993008924 A1 | 5/1993 |
| WO | 0066351 A2 | 11/2000 |
| WO | 02098572 A1 | 12/2002 |
| WO | 2011009913 A1 | 1/2011 |
| WO | WO2011083644 A1 | 7/2011 |

OTHER PUBLICATIONS

European Patent Office, International Search Report and Written Opinion in PCT Application Serial No. PCT/US2012/032893, dated Aug. 8, 2012.

European Patent Office, Written Opinion of the International Preliminary Examining Authority in PCT Application Serial No. PCT/US2012/032893, dated May 7, 2013.

European Patent Office, International Preliminary Report on Patentability in PCT Application Serial No. PCT/US2012/032893, dated Aug. 9, 2013.

European Patent Office, European Search Report in EP Application Serial No. 13163420.6, dated Feb. 4, 2015 (12 pages).

PCT Application No. PCT/US2015/043713, International Search Report and Written Opinion dated Nov. 24, 2015, 11 pages.

Chinese Application No. 201310125239.7: First Office Action dated Jun. 14, 2016, 6 pages.

European Patent Application No. 17157639.0: Extended European Search Report dated Jul. 3, 2017, 9 pages.

Japanese Patent Application No. 2013-082821: Notification of Reasons for Refusal dated May 22, 2017, 3 pages.

* cited by examiner

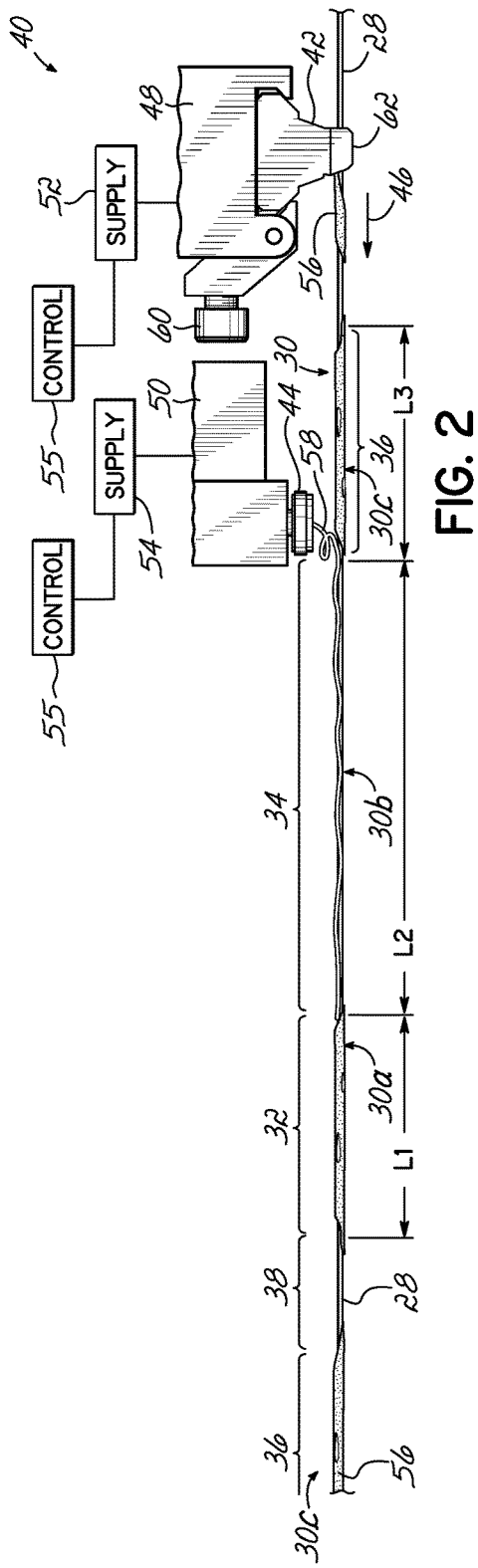
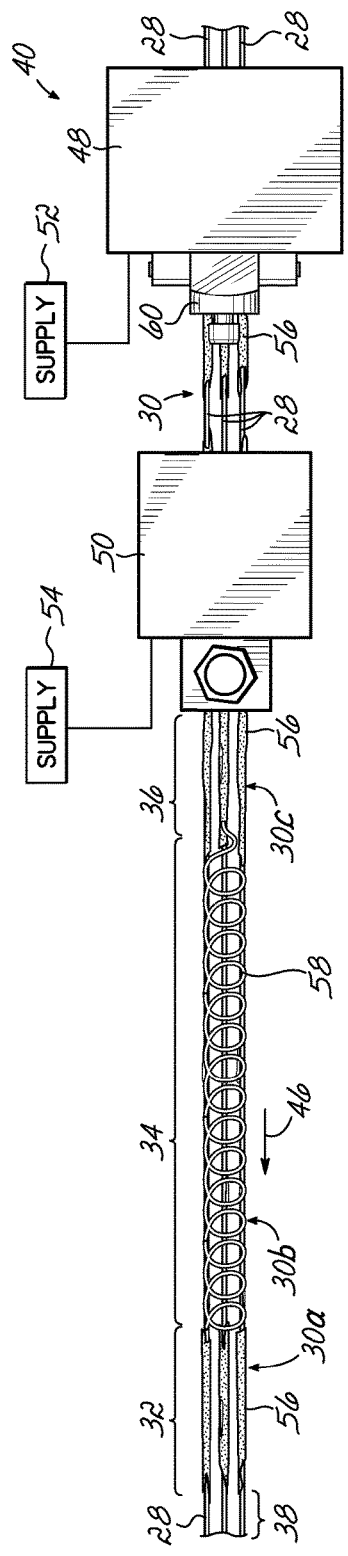
FIG. 2
FIG. 3

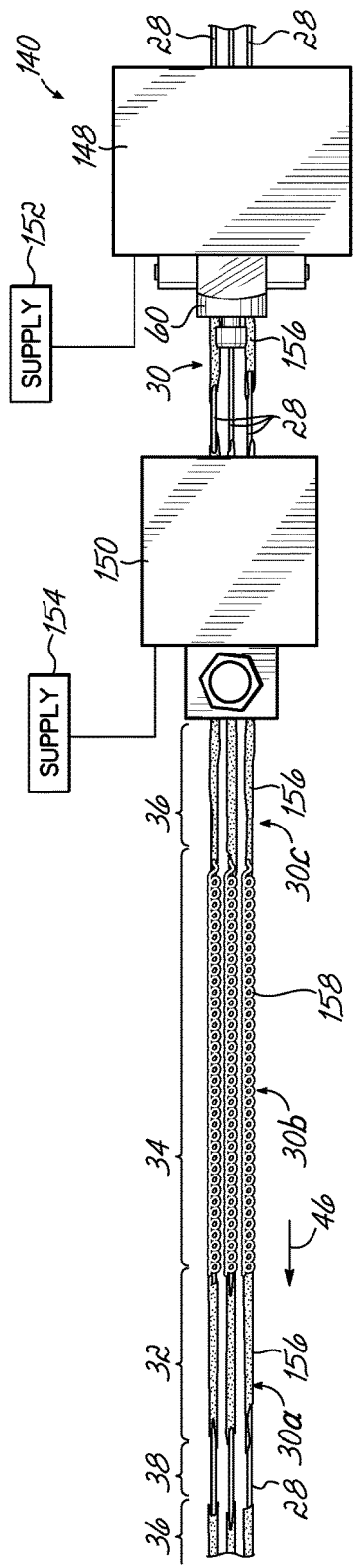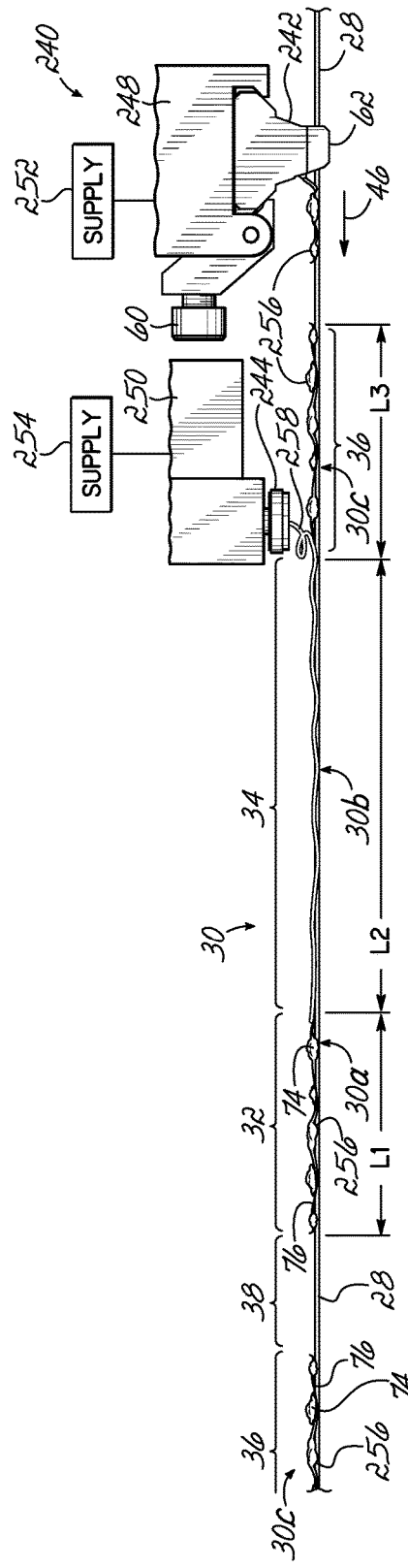

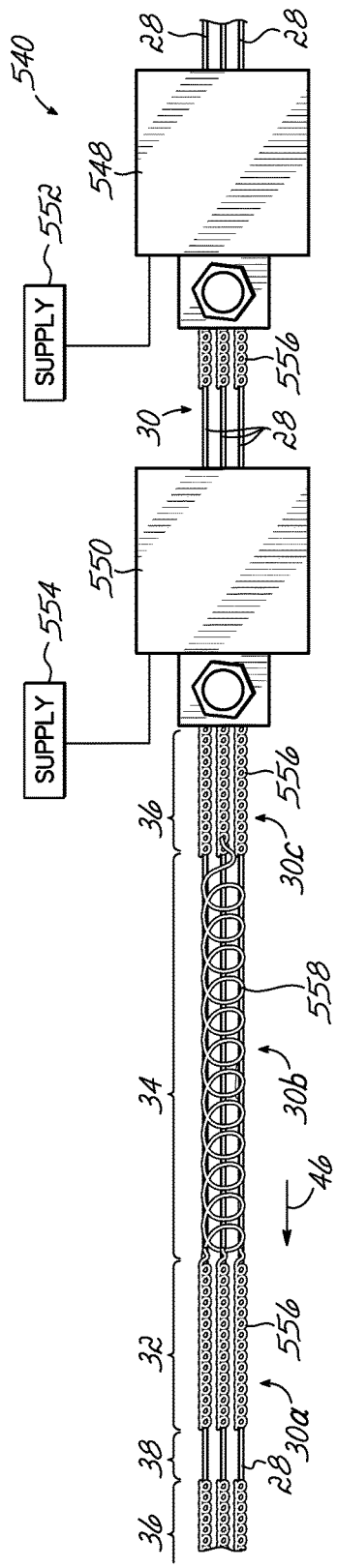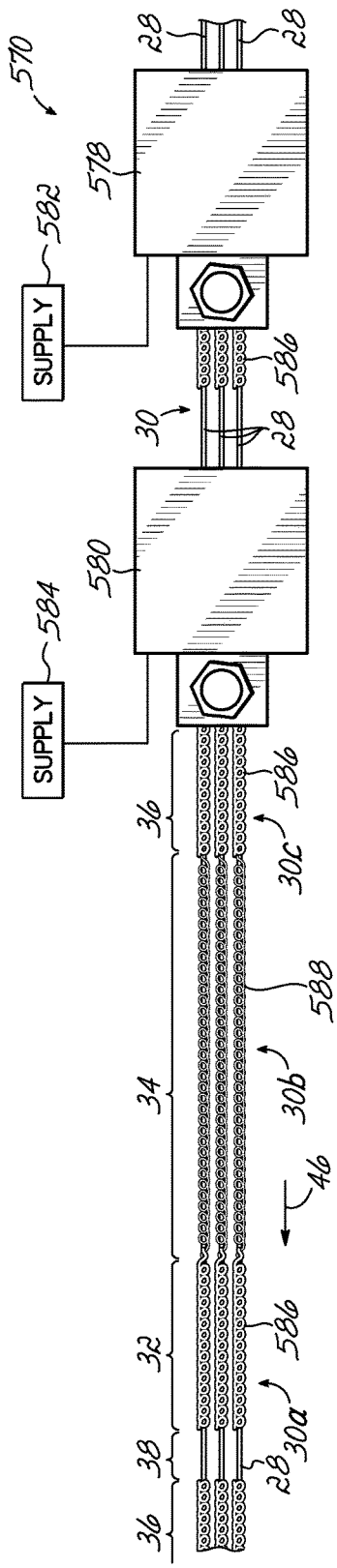

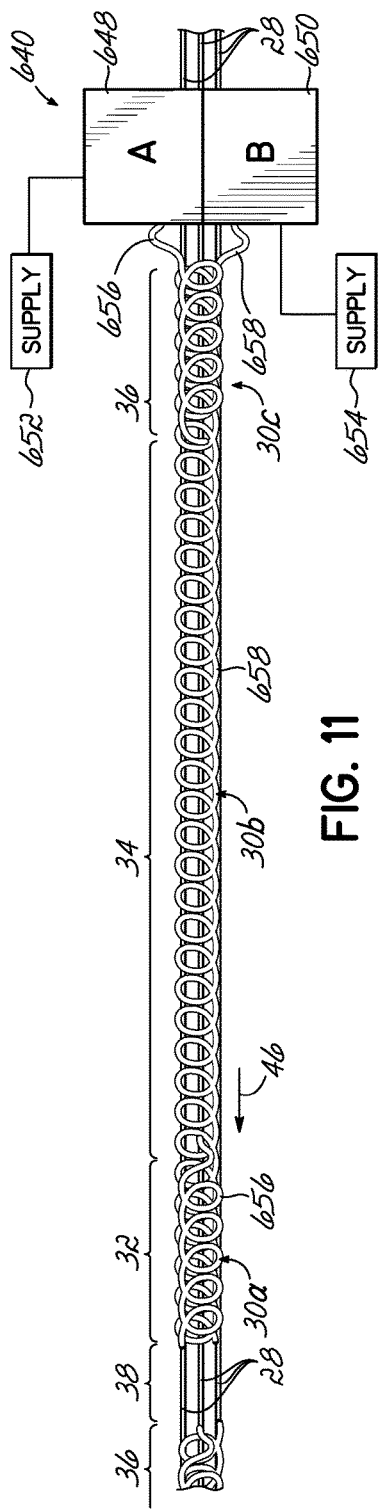
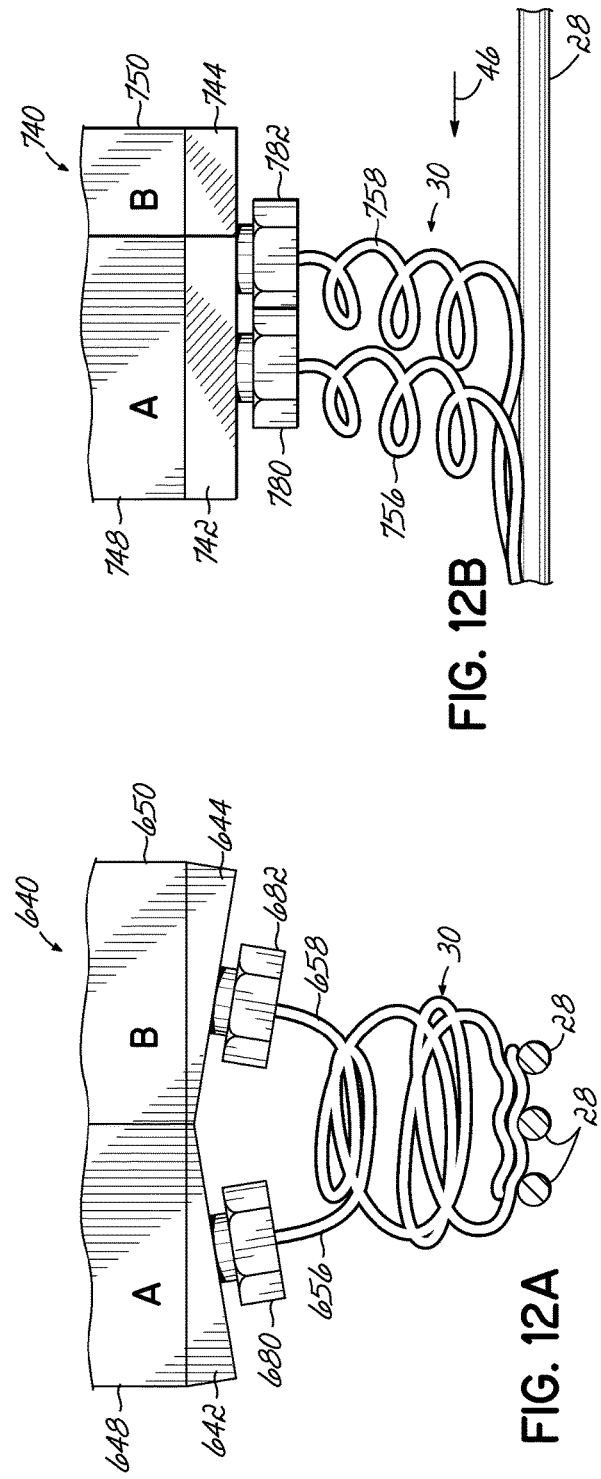

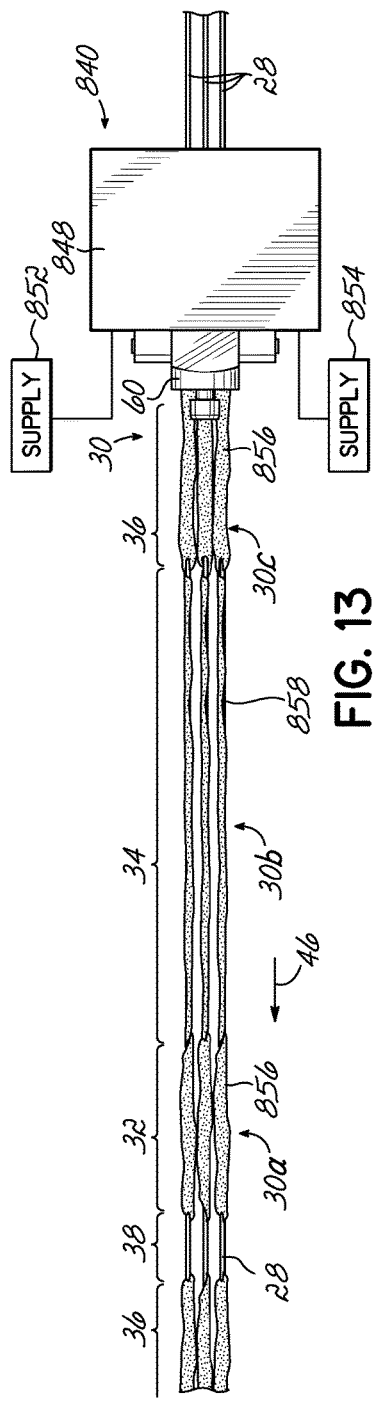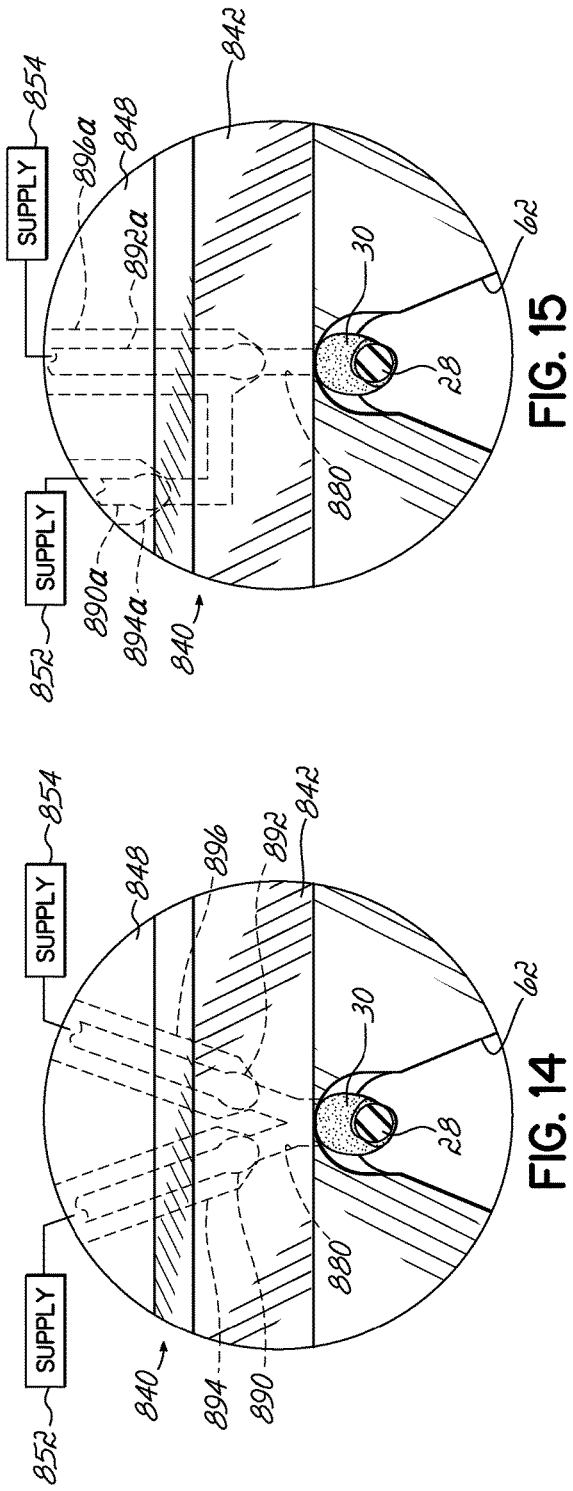
FIG. 13
FIG. 14
FIG. 15

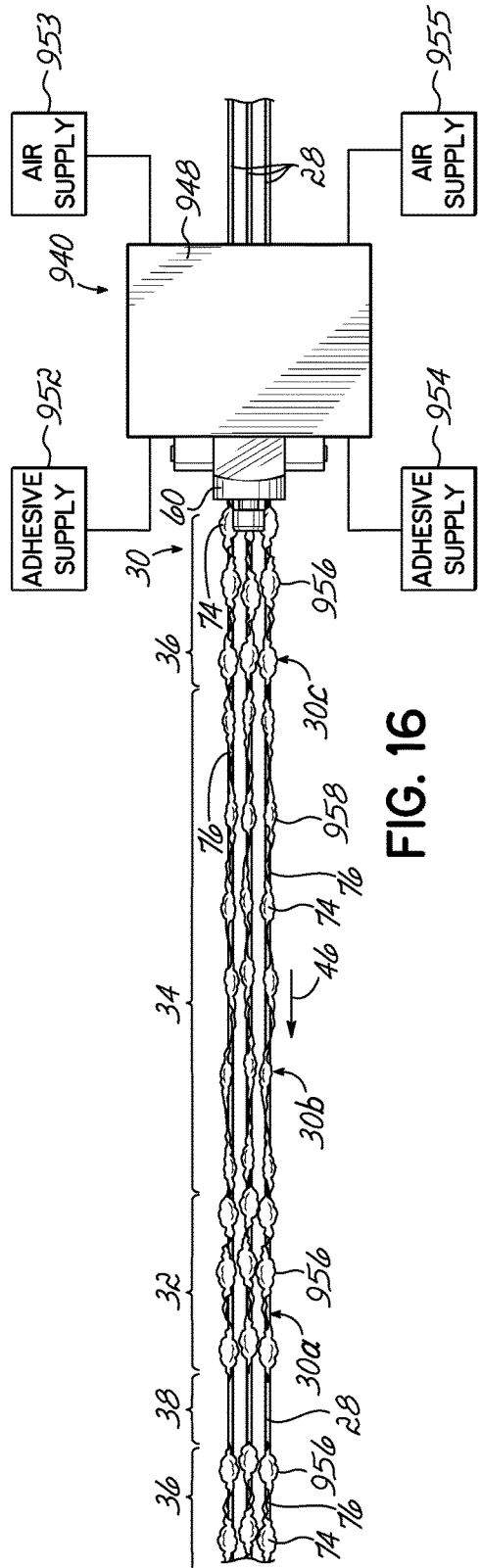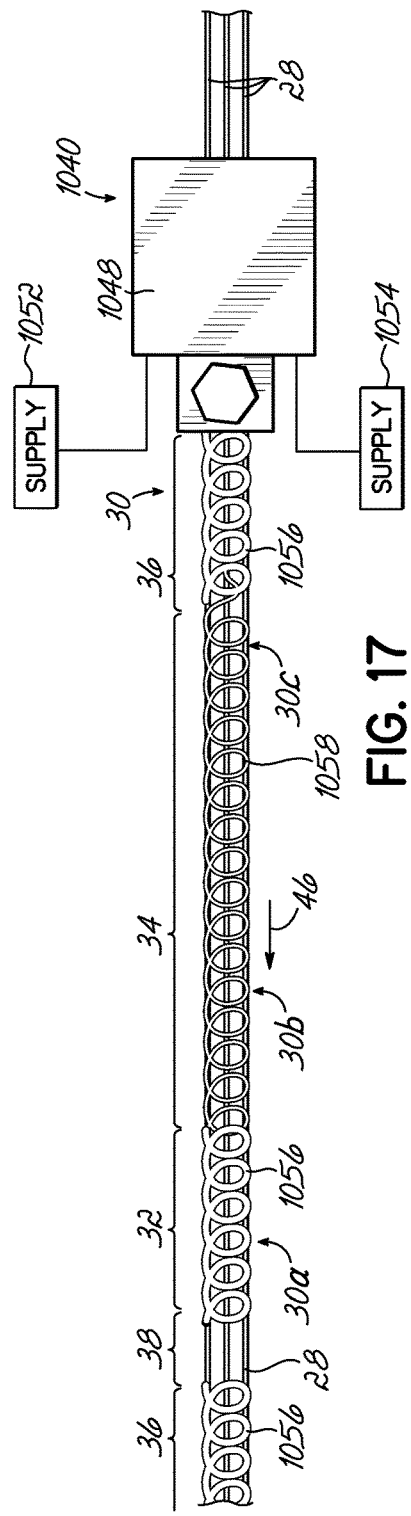

DISPENSING APPARATUS FOR APPLYING ADHESIVE ON AN ELASTIC STRAND IN ASSEMBLY OF A PERSONAL DISPOSABLE HYGIENE PRODUCT

CROSS REFERENCE TO RELATED APPLICATIONS

This application is a continuation application of U.S. patent application Ser. No. 14/456,418, filed on Aug. 11, 2014 (pending), which is a continuation-in-part application of U.S. patent application Ser. No. 13/444,126, filed on Apr. 11, 2012 (pending), the disclosures of which are incorporated by reference herein in their entireties.

TECHNICAL FIELD

The present invention generally relates to a method for dispensing adhesive and more particularly, to a method for dispensing adhesive onto at least one elastic strand during construction of a personal disposable hygiene product.

BACKGROUND

Liquid adhesive, such as hot melt adhesive, is applied onto various components during manufacture of disposable personal hygiene products such as diapers, adult incontinence products, and feminine hygiene products. Dispensing methods and systems have been developed for applying hot melt adhesive onto various components of the disposable personal hygiene product. In one example, these dispensing systems apply a hot melt adhesive filament to one or more stretched elastic strands, which are then adhered to a nonwoven substrate to form an elasticized portion of the disposable personal hygiene product. Downstream of the dispensing system, the various components (e.g., flat substrate layers and elastic strands) pass through a pressure nip to secure the components together.

Many disposable personal hygiene products include elasticized leg gathers adjacent to leg openings to secure the personal hygiene product against the user's legs and to contain any waste material captured by the personal disposable hygiene product. In these applications, a high level of creep resistance is desirable. "Creep" of an elastic strand is defined as the movement of either end of the elastic strand from an initial location where the end is adhered to a substrate. If an elastic strand undergoes any significant amount of creep after assembly, at least one end of the elastic strand will effectively de-bond from the substrate and reduce the ability of the elasticized portion to remain firmly engaged with the skin surface. To avoid this undesirable creep, a high quality bond must be formed by the adhesive applied to the elastic strand so that the elastic strand does not de-bond from the substrate.

One well understood method of improving the quality of an adhesive bond and thereby reducing creep is by applying additional adhesive on the substrate or the elastic strand(s). However, applying too much adhesive to the elastic strand locks the elastic strand along its length and thereby reduces the effectiveness of the elastic material to apply force to the substrate. In other words, the elastic strand loses the ability to apply sufficient retraction force to the substrate. Moreover, increasing the amount of adhesive used in disposable personal hygiene product manufacturing significantly increases cost and also reduces the "hand" or softness of the resulting product. Applying too much adhesive material may also lead to "burn through," which occurs when the adhesive material burns or melts through the adhered substrate. Consequently, the amount of adhesive used to adhere elastic strands to substrates should be minimized while also maintaining a high level of creep resistance, a high retraction force, and minimized burn through and stiffness.

However, conventional dispensing methods and systems for coating elastic strands in personal disposable hygiene products utilize a constant volume or coating of adhesive along the entire length of the elastic strand(s). As described above, the coating must be sufficient to prevent creep at the opposing ends of the elastic strand(s), and thus, the constant coating adds significant add on weight to the final personal disposable hygiene product. As described above, any excess adhesive add on is undesirable for multiple reasons, including reduced force retraction capability and softness and increased manufacturing cost.

There is a need, therefore, for an adhesive dispensing method and apparatus that addresses one or more of these difficulties and reduces the amount of adhesive used to form elasticized portions of personal disposable hygiene products.

SUMMARY

According to one embodiment of the invention, a method of dispensing adhesive onto a stretched elastic strand and manufacturing a personal disposable hygiene product includes moving the stretched elastic strand along a machine direction and dispensing a first, second, and third volume of adhesive onto the elastic strand by a single dispensing nozzle including first and second valves controlling flow from corresponding first and second adhesive supplies. The dispensing further includes opening the first valve while leaving the second valve closed to apply the first volume of adhesive onto a first portion of the elastic strand; closing the first valve to stop applying the first volume of adhesive; opening the second valve and keeping the first valve closed to apply the second volume of adhesive onto a second portion of the elastic strand located downstream from the first portion relative to the machine direction; closing the second valve to stop applying the second volume of adhesive; and opening the first valve and closing the second valve to apply the third volume of adhesive onto a third portion of the elastic strand located downstream from the second portion relative to the machine direction. The second volume is less than the first volume and less than the third volume. The method also includes contacting the stretched elastic strand with first and second substrate layers to adhesively secure the stretched elastic strand between the first and second substrate layers, and releasing the stretched elastic strand to allow the elastic strand to retract from a stretched condition, thereby collectively defining an elasticized portion of the hygiene product with the first and second substrate layers. When the elastic strand is adhered to the substrate, the first and third portions define opposing ends of the elastic strand and the second portion defines a central portion of the elastic strand extending between the opposing ends. The first and third volumes of adhesive are sufficient to limit movement of the opposing ends of the elastic strand while maintaining the bond under normal wear conditions for the hygiene product. The second volume of adhesive is sufficiently low to allow the elastic strand to retract from the stretched condition.

According to another embodiment, a method of dispensing adhesive onto at least one stretched elastic strand to be adhered to a substrate to form a personal disposable hygiene product includes moving the stretched elastic strand along a machine direction and applying a first volume of adhesive onto a first portion of the elastic strand. The method also includes applying a second volume of adhesive onto a second portion of the elastic strand located downstream from the first portion relative to the machine direction, and applying a third volume of adhesive onto a third portion of the elastic strand located downstream from the second portion relative to the machine direction. The second volume is less than the first volume and less than the third volume. When the elastic strand is adhered to the substrate, the first and third portions define opposing ends of the elastic strand and the second portion defines a central portion of the elastic strand extending between the opposing ends.

In one aspect, the first and third portions of the elastic strand collectively define a first length and the second portion of the elastic strand defines a second length longer than the first length. Thus, the second volume of adhesive is applied over a majority of the elastic strand. In another aspect, applying the first, second, and third volumes of adhesive includes dispensing a first quantity of adhesive onto the first and third portions of the elastic strand, and dispensing a second quantity of adhesive onto the first, second, and third portions of the elastic strand. The second quantity defines the second volume of adhesive on the second portion of the elastic strand. The first and second quantities collectively define the first volume of adhesive on the first portion of the elastic strand and the third volume of adhesive on the third portion of the elastic strand. Alternatively, applying the first, second, and third volumes of adhesive includes dispensing a first quantity of adhesive onto the first and third portions of the elastic strand and dispensing a second quantity of adhesive onto the second portion of the elastic strand. In this alternative, the first quantity of adhesive defines the first volume of adhesive on the first portion of the elastic strand and the third volume of adhesive on the third portion of the elastic strand, while the second quantity of adhesive defines the second volume on the second portion of the elastic strand.

The first and second quantities of adhesive may be dispensed simultaneously onto the first portion and then onto the third portion of the elastic strand, or one of the first and second quantities may be dispensed onto the elastic strand before the other quantity. In one example, the first and second quantities are dispensed by respective first and second dispensing nozzles, which are fed adhesive at first and second predetermined or adjustable flow rates.

In another aspect, the first, second, and third volumes of adhesive are dispensed by a single dispensing nozzle including first and second valves that control flow from corresponding first and second adhesive supplies. To this end, the first and second valves are opened to apply the first volume of adhesive to the first portion of the elastic strand. Closing the second valve while leaving the first valve open causes the second volume of adhesive to be applied to the second portion of the elastic strand. Opening the first and second valves causes the third volume of adhesive to be applied to the third portion of the elastic strand. In some embodiments with a single dispensing nozzle, adhesive is pumped at an adjustable first flow rate to the first valve and adhesive is pumped at an adjustable second flow rate to the second valve.

In another embodiment of the invention, a method of dispensing adhesive onto a plurality of stretched elastic strands to be adhered to a substrate to form a personal disposable hygiene product includes moving each of the stretched elastic strands along a machine direction. The method further includes applying a first volume of adhesive onto a first portion of each of the elastic strands, applying a second volume of adhesive onto a second portion of each of the elastic strands located downstream from the first portion, and applying a third volume of adhesive onto a third portion of each of the elastic strands located downstream from the second portion. The second volume is less than the first volume and less than the third volume. When the elastic strand is adhered to the substrate, the first and third portions define opposing ends of the elastic strand and the second portion defines a central portion of the elastic strand extending between the opposing ends. Applying the first, second, and third volumes of adhesive may include dispensing at least one quantity of adhesive individually onto each of the plurality of elastic strands, or dispensing at least one quantity of adhesive collectively onto all of the plurality of elastic strands.

In another embodiment, a personal disposable hygiene product includes a nonwoven substrate with first and second longitudinal sides. The hygiene product also includes first and second stretched elastic strands adhered to the nonwoven substrate respectively along the first and second longitudinal sides. Each of the elastic strands includes a first portion defining an end of the elastic strand, a second portion defining a central portion of the elastic strand, and a third portion defining another end of the elastic strand. The first portions are coated with a first volume of adhesive, the second portions are coated with a second volume of adhesive, and the third portions are coated with a third volume of adhesive. The second volume of adhesive is less than each of the first and third volumes of adhesive.

In yet another embodiment of the invention, a dispensing apparatus applies adhesive to at least one stretched elastic strand including first, second, and third portions along a length of the elastic strand that are to be adhered to a substrate to form a personal disposable hygiene product. The apparatus includes a first dispensing nozzle for dispensing a first volume of adhesive onto the stretched elastic strand at the first portion and for dispensing a third volume of adhesive onto the stretched elastic strand at the third portion. The apparatus also includes a second dispensing nozzle for dispensing a second volume of adhesive onto the stretched elastic strand at a second portion extending between the first and third portions. The second volume of adhesive is less than each of the first and third volumes of adhesive.

In one aspect, the first dispensing nozzle includes a strand guide, while the second dispensing nozzle does not include a strand guide. In one aspect, the dispensing nozzles may include the same type of dispensing nozzle or different types of dispensing nozzles. The dispensing apparatus also includes a first adhesive supply for pumping adhesive to the first dispensing nozzle, a second adhesive supply for pumping adhesive to the second dispensing nozzle, and a control for selectively actuating the first and second adhesive supplies.

In another embodiment, a dispensing apparatus applies adhesive to at least one stretched elastic strand including first, second, and third portions along a length of the elastic strand that are to be adhered to a substrate to form a personal disposable hygiene product. The apparatus includes a first dispensing nozzle for dispensing a first quantity of adhesive onto the stretched elastic strand at the first and third portions. The apparatus also includes a second dispensing nozzle for dispensing a second quantity of adhesive onto the stretched elastic strand at the first, second, and third portions. The first and second quantities of adhesive collectively define a first volume of adhesive on the first portion of the elastic strand and a third volume of adhesive on the third portion of the elastic strand. The second quantity of adhesive defines a second volume of adhesive on the second portion of the elastic strand that is less than each of the first and third volumes of adhesive.

In another embodiment of the invention, a dispensing apparatus applies adhesive to at least one stretched elastic strand that is to be adhered to a substrate to form a personal disposable hygiene product. The apparatus includes a single dispensing nozzle for dispensing adhesive onto the stretched elastic strand at first, second, and third portions located in sequence along the length of the elastic strand. The dispensing apparatus also includes a first valve adapted to control flow from a first adhesive supply through the dispensing nozzle and a second valve adapted to control flow from a second adhesive supply through the dispensing nozzle. The first and second valves are opened to apply a first volume of adhesive on the first portion or to apply a third volume of adhesive on the third portion. The first valve is opened while the second valve is closed to apply a second volume of adhesive on the second portion that is less than the first or third volumes of adhesive.

Various additional features and advantages of the invention will become more apparent to those of ordinary skill in the art upon review of the following detailed description of the illustrative embodiments taken in conjunction with the accompanying drawings.

BRIEF DESCRIPTION OF THE DRAWINGS

FIG. 2 is a schematic side view of a dispensing apparatus for applying adhesive to a plurality of stretched elastic strands according to one embodiment of the current invention.

FIG. 3 is a schematic top view of the dispensing apparatus of FIG. 2.

FIG. 4 is a schematic top view of another embodiment of a dispensing apparatus for applying adhesive to elastic strands.

FIG. 5 is a schematic side view of another embodiment of a dispensing apparatus for applying adhesive to elastic strands.

FIG. 9 is a schematic top view of yet another embodiment of a dispensing apparatus for applying adhesive to elastic strands.

FIG. 10 is a schematic top view of yet another embodiment of a dispensing apparatus for applying adhesive to elastic strands.

FIG. 11 is a schematic top view of another embodiment of a dispensing apparatus for applying adhesive to elastic strands, the dispensing apparatus including two nozzles in parallel.

FIG. 12A is a schematic front view of the dispensing apparatus of FIG. 11 during a dispensing operation.

FIG. 12B is a schematic side view of another embodiment of a dispensing apparatus similar to the dispensing apparatus of FIGS. 11 and 12A.

FIG. 13 is a schematic top view of yet another embodiment of a dispensing apparatus for applying adhesive to elastic strands.

FIG. 14 is a schematic front view of the dispensing apparatus of FIG. 13, showing a first set of valves in phantom.

FIG. 15 is a schematic front view of the dispensing apparatus of FIG. 13, showing a second set of valves in phantom.

FIG. 16 is a schematic top view of another embodiment of a dispensing apparatus for applying adhesive to elastic strands.

FIG. 17 is a schematic top view of yet another embodiment of a dispensing apparatus for applying adhesive to elastic strands.

DETAILED DESCRIPTION OF THE ILLUSTRATIVE EMBODIMENTS

Figure 1:
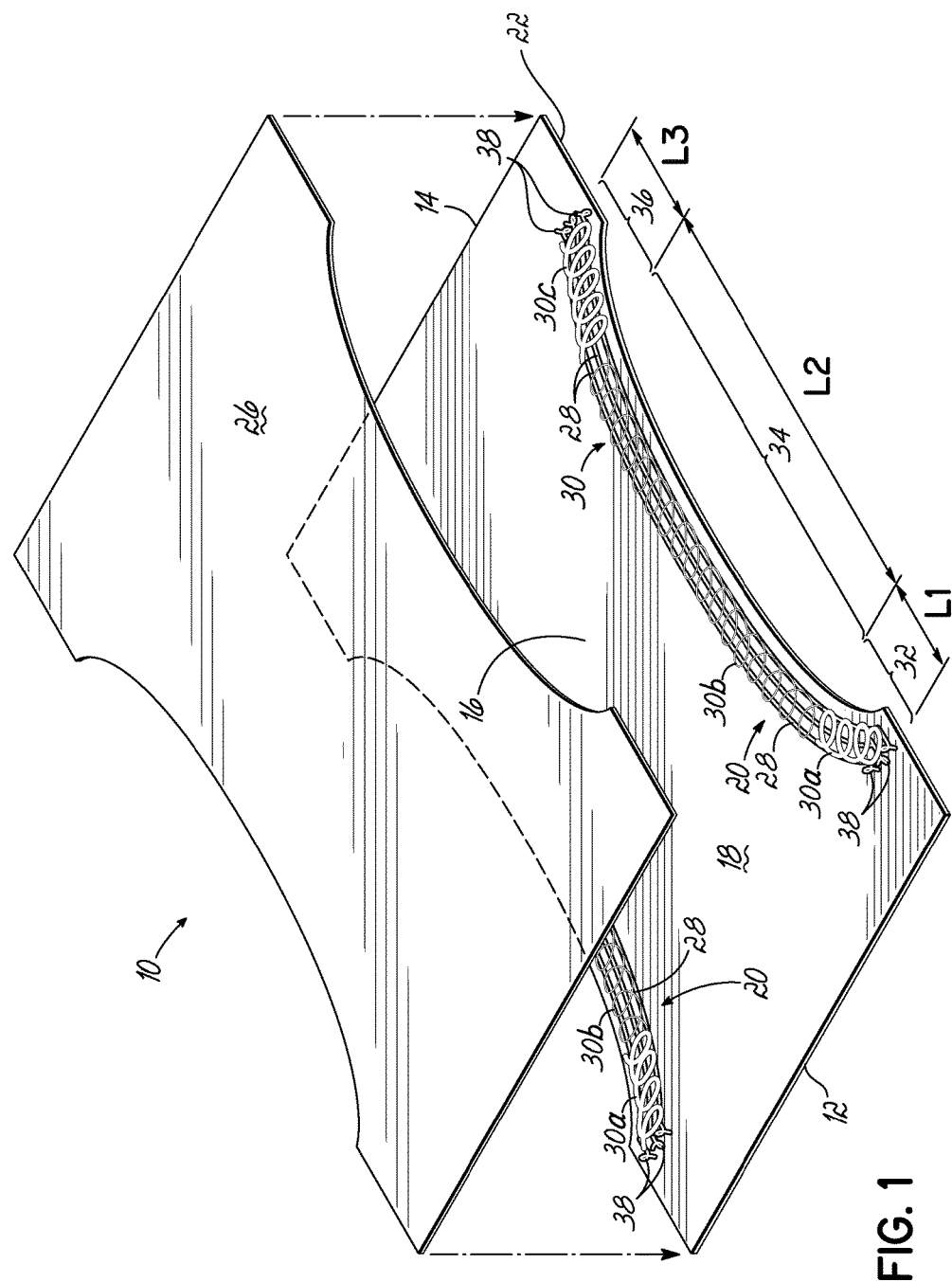
FIG. 1 is a partially exploded perspective view of a personal disposable hygiene product according to one embodiment of the current invention.

FIG. 1 illustrates one embodiment of a disposable personal hygiene product 10 manufactured using an exemplary method and apparatus of the invention. The disposable personal hygiene product 10 of this embodiment is a disposable diaper 10 including first and second ends 12, 14 configured to wrap around the waist of the user and a central portion 16 configured to extend between the legs of the user. The diaper 10 includes a flat nonwoven substrate 18, leg gathers 20 formed along each longitudinal side 22, 24 of the diaper 10 between the first and second ends 12, 14, and a second flat substrate 26 secured to the nonwoven substrate 18 to enclose the leg gathers 20. The second flat substrate 26 is another nonwoven substrate in the illustrated embodiment, although it will be understood that the elastic strands 28 may instead be sandwiched between (and adhesively secured with) two folded-over substrate layers of the same flat substrate in other embodiments consistent with the invention. The leg gathers 20 are formed by one or more elastic strands 28 that are secured to the nonwoven substrate 18 in a stretched condition so as to provide the diaper 10 with elasticity around the legs of the user, and the elasticity is provided when the elastic strands 28 are released to reduce tension in the elastic strands 28 and allow the elastic strands 28 to retract from a stretched condition following contacting and adhesive bonding to the substrate(s). The nonwoven substrate 18, leg gathers 20, and second substrate 26 are secured to each other with hot melt adhesive 30.

More particularly, each of the elastic strands 28 is advantageously adhered to the nonwoven substrate 18 by a varying amount of hot melt adhesive 30 applied along the length of the elastic strand 28. As described in further detail below, this varying amount of adhesive 30 may be applied by first and second dispensing nozzles in series, wherein the first dispensing nozzle may include a strand guide in some embodiments while the second dispensing nozzle cannot include a strand guide. To this end, each elastic strand 28 includes a first portion 32 adjacent the first end 12, a second portion 34 extending from the first portion 32 and adjacent the central portion 16, and a third portion 36 located adjacent to the second portion 34 and the second end 14. To this end, the first and third portions 32, 36 define opposing ends of the elastic strand 28 when adhered to the nonwoven substrate 18, while the second portion 34 defines a central portion of the elastic strand 28 during adherence. The first portion 32 is coated with a first volume of adhesive 30a, the second portion 34 is coated with a second volume of adhesive 30b, and the third portion 36 is coated with a third volume of adhesive 30c. The second volume of adhesive 30b is less than each of the first and third volumes of adhesive 30a, 30c. As well understood, the elastic strands 28 also include small free ends 38 beyond the first and second end portions 32, 34 that are not coated with adhesive 30 and thus retract or curl up when the remainder of the elastic strands 28 is adhered to the substrate 18. In the preceding and following description, the term "volume" is used as shorthand to describe an average volume of adhesive per unit length over the corresponding strand portion. Thus, the average volume of adhesive per unit length applied to the first and third portions 32, 36 of the elastic strand 28 is higher than the average volume of adhesive per unit length applied to the second portion 34.

With continued reference to FIG. 1, the higher first and second volumes of adhesive 30a, 30c along the first and third portions 32, 36 are schematically shown as a thicker spiral filament while a thinner spiral filament is shown at the second portion 34 to indicate the lessened second volume of adhesive 30b. It will be appreciated that the actual pattern applied to the elastic strands 28 may vary in other embodiments, such as by being applied as a plurality of discrete masses of adhesive that produce discrete bond points when adhering the elastic strands 28 to the nonwoven substrate 18. It will also be understood that while the volume per unit length is described as roughly constant over the entire length of a corresponding strand portion 32, 34, 36 in the exemplary embodiments below, the volume per unit length may vary over the length of one or more of the strand portions 32, 34, 36 without departing from the scope of the invention (i.e., as long as the "volume" or average volume per unit length remains lesser for the second portion 34 than the first and third portions 32, 36). In addition, the adhesive application patterns shown in FIG. 1 and the following figures on the elastic strands 28 are schematic artist's renderings of these patterns, as it will be understood that these patterns may vary in appearance significantly in a practical setting.

Also as shown in FIG. 1, the first portion 32 of the elastic strand 28 defines a first length L1, the second portion 34 defines a second length L2, and the third portion 36 defines a third length L3. The second length L2 is larger than the first and third lengths L1, L3 combined so that the second volume of adhesive 30b is applied over a majority of the total length of the elastic strand 28. Thus, the first and third volumes of adhesive 30a, 30c, each of which is high enough to produce a high quality bond with desirable creep resistance, are only applied onto the first and third portions 32, 36 of the elastic strand 28 where such a level of creep resistance is necessary. This higher average volume of adhesive per unit length is not used in the second portion 34 of the elastic strand 28 where creep resistance is less of a concern. Considering that this second portion 34 includes a majority of the elastic strand 28, the total amount of adhesive 30 used to adhere the elastic strand 28 to the substrate 18 is significantly reduced compared to a constant coating over the entire length of the elastic strand 28. Thus, the diaper 10 of this embodiment advantageously minimizes the amount of adhesive add on necessary to produce a high quality bond or construction of the various components of the diaper 10.

Turning to FIGS. 2 and 3, one embodiment of a dispensing apparatus 40 is shown for producing the disposable personal hygiene product 10 described above. The dispensing apparatus 40 includes a first dispensing nozzle 42 and a second dispensing nozzle 44 arranged in series along a machine direction indicated by arrow 46. The plurality of elastic strands 28 moves along the machine direction 46 past the first dispensing nozzle 42 and then past the second dispensing nozzle 44. The first and second dispensing nozzles 42, 44 operate to dispense hot melt adhesive 30 onto the elastic strands 28 so as to coat the elastic strands 28 with the first, second, and third volumes of adhesive 30a, 30b, 30c as described above. As described in further detail below, the elastic strands 28 run continuously through the dispensing apparatus 40 and are cut into separate elastic strands 28 downstream from the dispensing apparatus 40. To enable this cutting separation, the adjacent free ends 38 of two elastic strands 28 in series are not coated with any adhesive material. Consequently, each of the first and second dispensing nozzles 42, 44 cycles on and off repeatedly during operation of the dispensing apparatus 40.

In the illustrated embodiment, the first dispensing nozzle 42 is incorporated into a first dispensing module 48 and the second dispensing nozzle 44 is incorporated into a second dispensing module 50 separate from the first dispensing module 48. In this embodiment, the first dispensing module 48 includes a contact nozzle and the second dispensing module includes a non-contact nozzle, each nozzle being configured to apply a filament, bead, coating, or other amount of adhesive (hereinafter referred to as a "quantity") to the elastic strands 28. More specifically, the first dispensing nozzle 42 shown is a contact nozzle as described in U.S. patent application Ser. No. 61/474,129 to Saine, filed Apr. 11, 2011, which is assigned to the assignee of the current invention and the entire disclosure of which is hereby incorporated by reference herein. The second dispensing nozzle 44 shown is a non-contact swirl nozzle such as the Universal™ CF nozzle commercially available from Nordson Corporation of Westlake, Ohio, which is described in U.S. Pat. No. 4,785,996 to Ziecker et al., the entire disclosure of which is hereby incorporated by reference herein.

It will be understood that other types of non-contact nozzles (e.g., the Signature™ and Summitt™ Mini Swirl nozzles commercially available from Nordson Corporation of Westlake, Ohio) or other types of contact nozzles such as slot coaters may be used in other embodiments within the scope of this invention. Furthermore, even though the first and second dispensing nozzles 42, 44 are illustrated as different types of nozzles in this embodiment, it will be appreciated that the first dispensing nozzle 42 may be the same type of nozzle as the second dispensing nozzle 44 in other embodiments of the invention, assuming both dispensing nozzles 42, 44 are non-contact nozzles. Some of these alternatives are presented in further detail below with reference to FIGS. 4-12.

With continued reference to FIGS. 2 and 3, the first dispensing module 48 receives hot melt adhesive 30 from a first adhesive supply 52 and the second dispensing module 50 receives hot melt adhesive 30 from a second adhesive supply 54. The first and second adhesive supplies 52, 54 operate to pump heated liquid adhesive 30 to the first and second dispensing nozzles 42, 44. In one example, the first adhesive supply 52 includes a first individually adjustable pump 52 for supplying an adjustable flow of adhesive 30 to the first dispensing nozzle 42. The second adhesive supply 54 includes a second individually adjustable pump 54 separate from the first pump 52 for supplying another adjustable flow of adhesive 30 to the second dispensing nozzle 44. Alternatively, the first and second adhesive supplies 52, 54 may be first and second output streams of a common dual stream pump. In these embodiments with a dual stream pump, each adhesive supply 52, 54 delivers a predetermined flow of adhesive to each of the first and second dispensing nozzles 42, 44. Therefore, although the first and second adhesive supplies 52, 54 are illustrated as separate elements in FIGS. 2 and 3, it will be understood that the first and second adhesive supplies 52, 54 may be generated from a single dual stream pump or separate pumps without departing from the scope of the invention. Additionally, it will be understood that this and each of the following embodiments of the dispensing apparatus 40 may also include a control 55 for selectively actuating (e.g., turning on and off) the first and second adhesive supplies 52, 54.

The operation of the dispensing apparatus 40 is shown schematically in FIGS. 2 and 3. In this regard, the plurality of stretched, uncoated elastic strands 28 passes the first dispensing nozzle 42 while moving along the machine direction 46. The first dispensing nozzle 42 operates to dispense a first quantity 56 of adhesive onto each of the plurality of elastic strands 28. More specifically, a first quantity 56 is dispensed onto the first portion 32 and the third portion 36 of each elastic strand 28. As described in further detail in U.S. patent application Ser. No. 61/474,129 to Saine, the first quantity 56 is a quantity applied by contacting the elastic strand 28 with an extruded adhesive 30 and then blowing air onto the elastic strand 28 to spread the adhesive 30 around the elastic strand 28. As described briefly above, the elastic strands 28 are cut from a continuous elastic line stock downstream of the dispensing apparatus 40, so the first dispensing nozzle 42 cycles on and off to leave gaps with no adhesive 30 at the second portions 34 and at the free ends 38 between applications of adhesive to the first portions 32 and to the third portions 36.

In a similar manner, the plurality of elastic strands 28 coated with the first quantity 56 of adhesive then passes the second dispensing nozzle 44 while moving along the machine direction 46. The second dispensing nozzle 44 operates to dispense a second quantity 58 of adhesive onto the plurality of elastic strands 28 at the second portion 34. In this embodiment, the second quantity 58 is a filament forming a swirl pattern extending across all of the elastic strands 28. The second dispensing nozzle 44 is cycled on and off to apply the second quantity 58 onto the second portions 34 of the elastic strands 28, leaving the first and third portions 32, 36 and the free ends 38 substantially uncoated with the second quantity 58.

As shown schematically in FIGS. 2 and 3, the first quantity 56 of adhesive forms the first volume of adhesive 30*a* on the first portion 32 of each elastic strand 28 as well as the third volume of adhesive 30*c* on the third portion 36 of each elastic strand 28. The second quantity 58 of adhesive forms the second volume of adhesive 30*b* on the second portion 34 of each elastic strand 28. In this regard, the dispensing apparatus 40 operates to apply the first volume of adhesive 30*a* onto the first portion 32, apply the second volume of adhesive 30*b* onto the second portion 34, and apply the third volume of adhesive 30*c* onto the third portion 36. As described above, the first and third volumes of adhesive 30*a*, 30*c* are sufficient to provide a high quality bond with desirable creep resistance at the first and third portions 32, 36 of the elastic strands 28, while the second volume of adhesive 30*b* is less than the first or third volumes 30*a*, 30*c* of adhesive to advantageously minimize adhesive add on in the disposable personal hygiene product 10.

In one example, the first dispensing nozzle 42 is configured to dispense a coating that defines a volume (i.e., an average volume per unit length) of 0.2 g/m or 0.2 mg/mm on each elastic strand 28. The second dispensing nozzle 44 is configured to dispense a coating that defines a volume of 0.1 g/m or 0.1 mg/mm on each elastic strand 28. As a result, the first and third portions 32, 36 are coated with an equal volume of 0.2 mg/mm, while the second portion 34 is coated with a volume of 0.1 mg/mm. In other words, the first and third volumes of adhesive 30*a*, 30*c* are equivalent to 0.2 mg/mm and the second volume of adhesive 30*b* is equivalent to 0.1 mg/mm. Assuming approximate lengths of L1=L3=50 mm for the first and third portions 32, 36 and L2=300 mm for the second portion 34, the total adhesive add on per elastic strand is 50 mg of adhesive: (0.2 mg/mm)*(50 mm)=10 mg for each of the first and third portions 32, 36; plus (0.1 mg/mm)*(300 mm)=30 mg for the second portion 34.

By contrast, a conventional constant volume coating having the same bond strength at the first and third portions 32, 36 would require a volume of 0.2 mg/mm over the entire 400 mm length of the elastic strand, which equates to 80 mg of adhesive add on per strand. Thus, the dispensing apparatus 40 of the current invention advantageously reduces the adhesive add on by nearly 40% in this example compared to an analogous conventional coating. It will be understood that the relative values of the first, second, and third volumes 30*a*, 30*b*, 30*c* and the relative lengths of the strand portions 32, 34, 36 may be modified in other examples within the scope of the invention to produce adhesive savings of 40%-60% or even more, depending on the application. This level of adhesive reduction significantly reduces the manufacturing cost for each disposable personal hygiene product 10 and increases the hand or softness of the product 10 while maintaining the same high quality bonds as in conventional methods and dispensing apparatuses.

The first and second dispensing nozzles 42, 44 are controlled by internal valves (not shown in this embodiment) in the first and second dispensing modules 48, 50, as well understood in the art. These valves are operable to cycle on and off for the required lengths of time to dispense the first and second quantities 56, 58 onto enough continuous elastic strand stock to form 400-1500 products (diapers) per minute. Assuming the same portion lengths as described above with a 25 mm gap defining the free ends 38, the valves would operate as follows for producing 500 products (diapers) per minute. The valve of the first dispensing module 48 would open for about 14 milliseconds to apply adhesive 30 to each first portion 32 and each third portion 36, separated by closed times of about 85 milliseconds for each second portion 34 and about 7 milliseconds for each free end 38 location. The valve of the second dispensing module 50 would open for about 85 milliseconds to apply adhesive 30 to each second portion 34, separated by closed times of about 35 milliseconds for the other portions 32, 36, 38 of the elastic strands 28. It will be understood that the cycling rates of the valves may be modified in other embodiments without departing from the scope of the invention.

As described in further detail in U.S. patent application Ser. No. 61/474,129 to Saine, the first dispensing nozzle 42 may be connected to the first dispensing module 48 by a clamping mechanism 60 or a similar device. The first dispensing nozzle 42 defines a strand guide portion 62 for guiding each of the elastic strands 28 past the corresponding air and adhesive outlets (not shown) of the first dispensing nozzle 42. These strand guide portions 62 also align the plurality of strands 28 for passage under the air and adhesive outlets (not shown) of the second dispensing nozzle 44 because the second dispensing nozzle 44 cannot include a strand guide portion (e.g., such a strand guide portion would strip adhesive from the first dispensing nozzle 42 from the elastic strands 28). Further details of each of the first and second dispensing nozzles 42, 44 of this embodiment are described in the corresponding documents incorporated by reference above, and thus no further explanation of structure is provided here. It will be understood that in this and other embodiments described below, the first dispensing nozzle 42 may selectively include a strand guide portion 62, but the second dispensing nozzle 44 will not include a strand guide portion 62, regardless of the type of dispensing nozzles used in those embodiments. Examples of this arrangement are shown in FIGS. 2 and 5.

Although the embodiment of the dispensing apparatus 40 shown in FIGS. 2 and 3 is an exemplary embodiment of a dispensing apparatus for applying varying volumes of adhesive along the length of elastic strands 28, several modifications to the apparatus are also included within the scope of the current invention. With reference to FIG. 4, another embodiment of a dispensing apparatus 140 for applying varying volumes of adhesive along the length of elastic strands 28 in accordance with the invention is shown. Similar to the previous embodiment, the dispensing apparatus 140 shown in FIG. 4 includes a first dispensing module 148 and a second dispensing module 150 arranged in series along the machine direction 46. The first dispensing module 148 of this embodiment includes a contact nozzle as described in U.S. patent application Ser. No. 61/474,129 to Saine. The second dispensing module 150 of this embodiment includes a non-contact swirl nozzle such as the Summitt™ Mini Swirl nozzle commercially available from Nordson Corporation of Westlake, Ohio, which is described in U.S. Pat. No. 4,815,660 to Boger, the entire disclosure of which is hereby incorporated by reference herein.

More particularly, and as described in further detail in U.S. patent application Ser. No. 61/474,129 to Saine, the first dispensing module 148 applies a first quantity 156 of adhesive, which is a quantity applied by contacting the elastic strand 28 with an extruded adhesive 30 and then blowing air onto the elastic strand 28 to spread the adhesive 30 around the elastic strand 28. The second dispensing module 150 applies a second quantity 158 of adhesive, which is a miniature swirled filament of adhesive 30, onto each elastic strand 28 individually. Thus, unlike the previous embodiment, each of the first and second dispensing modules 148, 150 in this embodiment apply adhesive 30 individually onto each elastic strand 28.

As shown in FIG. 4, the first and second dispensing modules 148, 150 receive adhesive material from corresponding adhesive supplies 152, 154. Similar to the embodiments described above, the adhesive supplies 152, 154 may include separate individually adjustable pumps for each dispensing module 148, 150 or a shared dual stream pump for both dispensing modules 148, 150. Similar to the previous embodiment, the first dispensing module 148 dispenses the first quantity 156 onto the first and third portions 32, 36 of the elastic strands 28, while the second dispensing module 150 dispenses the second quantity 158 onto the second portions 34 of the elastic strands 28 only. Thus, as shown by the adhesive patterns shown in FIG. 4, the first and third portions 32, 36 are coated with first and third volumes of adhesive 30a, 30c that are larger than a second volume of adhesive 30b coating the second portions 34. As with the previously described embodiment, the dispensing apparatus 140 advantageously applies a higher volume of adhesive 30 to the end portions 32, 36 of the elastic strands 28 than to the central portions 34, thereby significantly reducing adhesive use while maintaining similar high bond quality.

Figure 6:
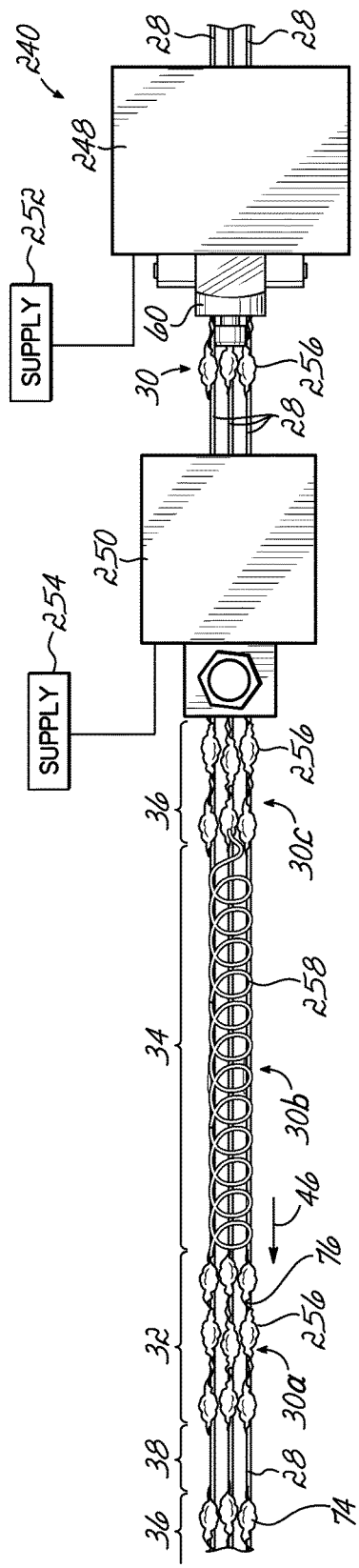
FIG. 6 is a schematic top view of the dispensing apparatus of FIG. 5.

With reference to FIGS. 5 and 6, another embodiment of a dispensing apparatus 240 for applying varying volumes of adhesive along the length of elastic strands 28 in accordance with the invention is shown. Similar to the previous embodiment, the dispensing apparatus 240 shown in FIGS. 5 and 6 includes a first dispensing module 248 and a second dispensing module 250 arranged in series along the machine direction 46. The first dispensing module 248 of this embodiment includes a first dispensing nozzle 242 that is a SureWrap® nozzle commercially available from Nordson Corporation of Westlake, Ohio, which is described in U.S. Pat. No. 7,578,882 to Harris et al., the entire disclosure of which is hereby incorporated by reference herein. The second dispensing module 250 of this embodiment includes a second dispensing nozzle such as the Universal™ CF nozzle commercially available from Nordson Corporation of Westlake, Ohio.

More particularly, and as described in further detail in U.S. Pat. No. 7,578,882 to Harris, the first dispensing nozzle 242 applies a first quantity 256 of adhesive formed by a filament impacted by a plurality of air jets to each elastic strand 28. The elastic strands 28 move faster than the first quantity 256 of adhesive, which causes the quantity 256 to stretch out during application onto the strands 28. As shown in FIGS. 5 and 6, this stretching of the first quantity 256 tends to separate or break the adhesive 30 into discrete localized increased masses 74 on the strands 28 that are separated from one another by thinner areas 76 of adhesive 30 running between adjacent masses 74. It will be understood that the thinner areas 76 may also break between adjacent increased masses 74, leaving no adhesive 30 between adjacent masses 74. Each of these discrete masses 74 of adhesive becomes a discrete bond point when the elastic strands 28 are adhered to the substrate 18. The second dispensing nozzle 244 applies a second quantity 258 of adhesive, which is a swirled filament of adhesive 30, onto all of the elastic strands 28 collectively. Thus, unlike the previous embodiment, the first dispensing nozzle 242 applies adhesive individually onto each elastic strand 28, while the second dispensing nozzle 244 applies adhesive collectively onto all of the elastic strands 28.

As shown in FIGS. 5 and 6, the first and second dispensing modules 248, 250 receive adhesive material from corresponding adhesive supplies 252, 254. Similar to the embodiments described above, the adhesive supplies 252, 254 may include separate individually adjustable pumps for each dispensing module 248, 250 or a shared dual stream pump for both dispensing modules 248, 250. Similar to the previous embodiment, the first dispensing nozzle 242 dispenses the first quantity 256 onto the first and third portions 32, 36 of the elastic strands 28, while the second dispensing nozzle 244 dispenses the second quantity 258 onto the second portions 34 of the elastic strands 28 only. Thus, as shown by the adhesive patterns shown in FIGS. 5 and 6, the first and third portions 32, 36 are coated with first and third volumes of adhesive 30a, 30c that are larger than a second volume of adhesive 30b coating the second portions 34. As with the previously described embodiment, the dispensing apparatus 240 advantageously applies a higher volume of adhesive 30 to the end portions 32, 36 of the elastic strands 28 than to the central portions 34, thereby significantly reducing adhesive use while maintaining similar high bond quality.

Figure 7:
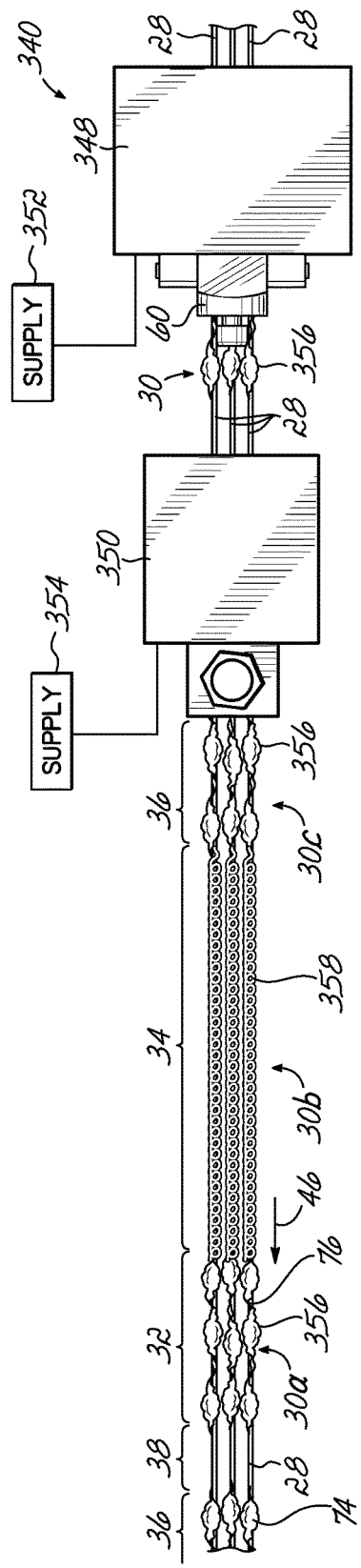
FIG. 7 is a schematic top view of yet another embodiment of a dispensing apparatus for applying adhesive to elastic strands.

With reference to FIG. 7, yet another embodiment of a dispensing apparatus 340 for applying varying volumes of adhesive along the length of elastic strands 28 in accordance with the invention is shown. Similar to the previous embodiment, the dispensing apparatus 340 shown in FIG. 7 includes a first dispensing module 348 and a second dispensing module 350 arranged in series along the machine direction 46. The first dispensing module 348 of this embodiment includes a SureWrap® nozzle commercially available from Nordson Corporation of Westlake, Ohio, which is described in U.S. Pat. No. 7,578,882 to Harris et al. The second dispensing module 350 of this embodiment includes a non-contact swirl nozzle such as the Summitt™ Mini Swirl nozzle commercially available from Nordson Corporation of Westlake, Ohio, which is described in U.S. Pat. No. 4,815,660 to Boger.

More particularly, and as described in further detail in U.S. Pat. No. 7,578,882 to Harris, the first dispensing module 348 applies a first quantity 356 of adhesive formed by a filament impacted by a plurality of air jets to each elastic strand 28. The elastic strands 28 move faster than the first quantity 356 of adhesive, which causes the first quantity 356 to stretch out during application into discrete localized increased masses 74 on the strands 28 that are separated from one another by thinner (or broken) areas 76 of adhesive 30 running between adjacent masses 74. The second dispensing module 350 applies a second quantity 358 of adhesive, which is a miniature swirled filament of adhesive 30, onto each elastic strand 28 individually. Thus, unlike the previous embodiment, each of the first and second dispensing modules 348, 350 in this embodiment apply adhesive 30 individually onto each elastic strand 28.

As shown in FIG. 7, the first and second dispensing modules 348, 350 receive adhesive material from corresponding adhesive supplies 352, 354. Similar to the embodiments described above, the adhesive supplies 352, 354 may include separate individually adjustable pumps for each dispensing module 348, 350 or a shared dual stream pump for both dispensing modules 348, 350. Similar to the previous embodiment, the first dispensing module 348 dispenses the first quantity 356 onto the first and third portions 32, 36 of the elastic strands 28, while the second dispensing module 350 dispenses the second quantity 358 onto the second portions 34 of the elastic strands 28 only. Thus, as shown by the adhesive patterns shown in FIG. 7, the first and third portions 32, 36 are coated with first and third volumes of adhesive 30a, 30c that are larger than a second volume of adhesive 30b coating the second portions 34. As with the previously described embodiment, the dispensing apparatus 340 advantageously applies a higher volume of adhesive 30 to the end portions 32, 36 of the elastic strands 28 than to the central portions 34, thereby significantly reducing adhesive use while maintaining similar high bond quality.

Figure 8:
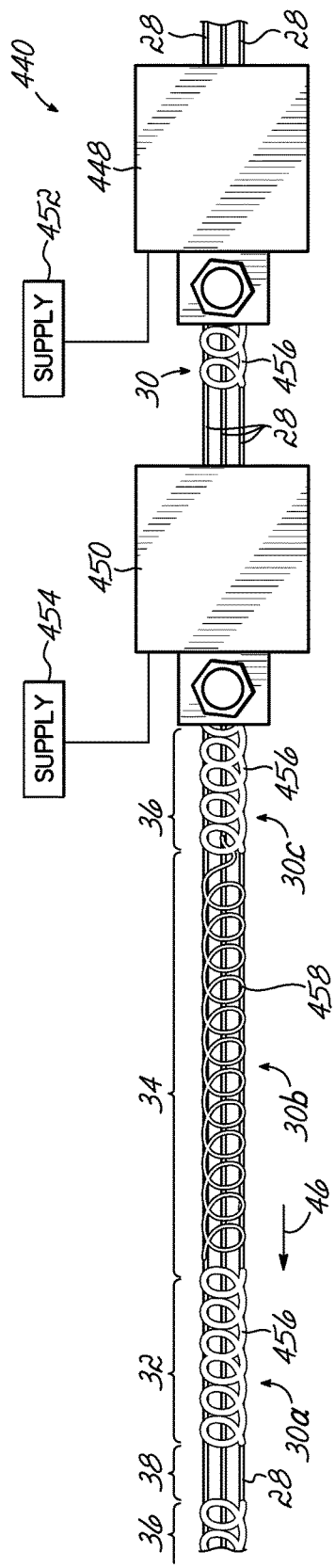
FIG. 8 is a schematic top view of another embodiment of a dispensing apparatus for applying adhesive to elastic strands.

With reference to FIG. 8, another embodiment of a dispensing apparatus 440 for applying varying volumes of adhesive along the length of elastic strands 28 in accordance with the invention is shown. Similar to the previous embodiment, the dispensing apparatus 440 shown in FIG. 8 includes a first dispensing module 448 and a second dispensing module 450 arranged in series along the machine direction 46. The first dispensing module 448 of this embodiment includes a non-contact swirl nozzle such as the Universal™ CF nozzle commercially available from Nordson Corporation of Westlake, Ohio. The second dispensing module 450 of this embodiment also includes a non-contact swirl nozzle such as the Universal™ CF nozzle commercially available from Nordson Corporation of Westlake, Ohio.

More particularly, the first dispensing module 448 applies a first quantity 456 of adhesive which is formed by a filament swirled by air jets onto all of the elastic strands 28 collectively. Similarly, the second dispensing module 450 applies a second quantity 458 of adhesive which is formed by a filament swirled by air jets onto all of the elastic strands 28 collectively. Thus, unlike the previous embodiment, each of the first and second dispensing modules 448, 450 in this embodiment apply adhesive 30 collectively onto all of the elastic strands 28.

As shown in FIG. 8, the first and second dispensing modules 448, 450 receive adhesive material from corresponding adhesive supplies 452, 454. Similar to the embodiments described above, the adhesive supplies 452, 454 may include separate individually adjustable pumps for each dispensing module 448, 450 or a shared dual stream pump for both dispensing modules 448, 450. Similar to the previous embodiment, the first dispensing module 448 dispenses the first quantity 456 onto the first and third portions 32, 36 of the elastic strands 28, while the second dispensing module 450 dispenses the second quantity 458 onto the second portions 34 of the elastic strands 28. Thus, as shown by the thicker and thinner adhesive patterns shown in FIG. 8, the first and third portions 32, 36 are coated with first and third volumes of adhesive 30a, 30c that are larger than a second volume of adhesive 30b coating the second portions 34. As with the previously described embodiment, the dispensing apparatus 440 advantageously applies a higher volume of adhesive 30 to the end portions 32, 36 of the elastic strands 28 than to the central portions 34, thereby significantly reducing adhesive use while maintaining similar high bond quality.

With reference to FIG. 9, yet another embodiment of a dispensing apparatus 540 for applying varying volumes of adhesive along the length of elastic strands 28 in accordance with the invention is shown. Similar to the previous embodiment, the dispensing apparatus 540 shown in FIG. 9 includes a first dispensing module 548 and a second dispensing module 550 arranged in series along the machine direction 46. The first dispensing module 548 of this embodiment includes a non-contact swirl nozzle such as the Summitt™ Mini Swirl nozzle commercially available from Nordson Corporation of Westlake, Ohio. The second dispensing module 550 of this embodiment includes a non-contact swirl nozzle such as the Universal™ CF nozzle commercially available from Nordson Corporation of Westlake, Ohio.

More particularly, the first dispensing module 548 applies a first quantity 556 of adhesive, which is a miniature swirled filament of adhesive 30, onto each elastic strand 28 individually. The second dispensing module 550 applies a second quantity 558 of adhesive, which is formed by a filament swirled by air jets onto all of the elastic strands 28 collectively. Thus, unlike the previous embodiment, the first dispensing module 548 applies adhesive collectively onto all of the elastic strands 28, while the second dispensing module 550 applies adhesive individually onto each elastic strand 28.

As shown in FIG. 9, the first and second dispensing modules 548, 550 receive adhesive material from corresponding adhesive supplies 552, 554. Similar to the embodiments described above, the adhesive supplies 552, 554 may include separate individually adjustable pumps for each dispensing module 548, 550 or a shared dual stream pump for both dispensing modules 548, 550. Similar to the previous embodiment, the first dispensing module 548 dispenses the first quantity 556 onto the first and third portions 32, 36 of the elastic strands 28, while the second dispensing module 550 dispenses the second quantity 558 onto the second portions 34 of the elastic strands 28. Thus, as shown by the adhesive patterns shown in FIG. 9, the first and third portions 32, 36 are coated with first and third volumes of adhesive 30a, 30c that are larger than a second volume of adhesive 30b coating the second portions 34. As with the previously described embodiment, the dispensing apparatus 540 advantageously applies a higher volume of adhesive 30 to the end portions 32, 36 of the elastic strands 28 than to the central portions 34, thereby significantly reducing adhesive use while maintaining similar high bond quality.

With reference to FIG. 10, another embodiment of a dispensing apparatus 570 for applying varying volumes of adhesive along the length of elastic strands 28 in accordance with the invention is shown. Similar to the previous embodiment, the dispensing apparatus 570 shown in FIG. 10 includes a first dispensing module 578 and a second dispensing module 580 arranged in series along the machine direction 46. The first dispensing module 578 of this embodiment includes a non-contact swirl nozzle such as the Summitt™ Mini Swirl nozzle commercially available from Nordson Corporation of Westlake, Ohio. The second dispensing module 580 of this embodiment also includes a non-contact swirl nozzle such as the Summitt™ Mini Swirl nozzle commercially available from Nordson Corporation of Westlake, Ohio.

More particularly, the first dispensing module 578 applies a first quantity 586 of adhesive, which is a miniature swirled filament of adhesive 30, onto each elastic strand 28 individually. The second dispensing module 580 applies a second quantity 588 of adhesive, which is a miniature swirled filament of adhesive 30, onto each elastic strand 28 individually. Thus, unlike the previous embodiment, each of the first dispensing module 578 and the second dispensing module 580 applies adhesive individually onto each elastic strand 28.

As shown in FIG. 10, the first and second dispensing modules 578, 580 receive adhesive material from corresponding adhesive supplies 582, 584. Similar to the embodiments described above, the adhesive supplies 582, 584 may include separate individually adjustable pumps for each dispensing module 578, 580 or a shared dual stream pump for both dispensing modules 578, 580. Similar to the previous embodiment, the first dispensing module 578 dispenses the first quantity 586 onto the first and third portions 32, 36 of the elastic strands 28, while the second dispensing module 580 dispenses the second quantity 588 onto the second portions 34 of the elastic strands 28. Thus, as shown by the adhesive patterns shown in FIG. 10, the first and third portions 32, 36 are coated with first and third volumes of adhesive 30a, 30c that are larger than a second volume of adhesive 30b coating the second portions 34. As with the previously described embodiment, the dispensing apparatus 570 advantageously applies a higher volume of adhesive 30 to the end portions 32, 36 of the elastic strands 28 than to the central portions 34, thereby significantly reducing adhesive use while maintaining similar high bond quality.

FIGS. 11 and 12A show another embodiment of a dispensing apparatus 640 according to the invention. In this dispensing apparatus 640, a first dispensing module 648 and a second dispensing module 650 are arranged generally in parallel along the machine direction 46 defined by the movement of the elastic strands 28. The first and second dispensing modules 648, 650 include corresponding first and second dispensing nozzles 642, 644 that are non-contact swirl nozzles such as the Universal™ CF nozzle commercially available from Nordson Corporation of Westlake, Ohio. Thus, the first and second dispensing nozzles 642, 644 apply respective first and second quantities 656, 658 of adhesive simultaneously onto the first portion 32 and then the third portion 36 of the plurality of elastic strands 28. In contrast to previous embodiments, the first dispensing nozzle 642 dispenses the first quantity 656 onto the first and third portions 32, 36 of the strands 28, while the second dispensing nozzle 644 dispenses the second quantity 658 onto the first, second, and third portions 32, 34, 36. Thus, as shown schematically by the overlaid spiral patterns in FIG. 11, the first and third portions 32, 36 are coated with first and third volumes of adhesive 30a, 30c, respectively, that are larger than a second volume of adhesive 30b coating the second portion 34. It will be understood that any of the embodiments of the dispensing apparatus shown herein may dispense overlapping quantities of adhesive 30 onto the first and third portions 32, 36 as shown in FIGS. 11 and 12A, or may dispense a completely separate first quantity on the first and third portions 32, 36 and a second quantity on the second portions 34 as shown in FIGS. 2 through 10.

Similar to the previous embodiment, the first dispensing nozzle 642 receives adhesive material pumped from a first adhesive supply 652 and the second dispensing nozzle 644 receives adhesive material pumped from a second adhesive supply 654. As described above, these first and second adhesive supplies 652, 654 may be separate individually adjustable pumps or may be the two output streams of a single dual stream pump. It will be understood that the first and second dispensing nozzles 642, 644 may be the same type of dispensing nozzle or different types of dispensing nozzles in various embodiments in accordance with the invention.

The simultaneous dispensing of the first and second quantities 656, 658 of adhesive is schematically shown from a front view in FIG. 12A. Each of the first and second dispensing nozzles 642, 644 may include corresponding first and second adhesive outlets 680, 682 that are angled slightly towards one another. As a result, the first and second quantities 656, 658 may entangle together slightly as they swirl towards the plurality of elastic strands 28. However, it will be appreciated that such entanglement of the quantities 656, 658 is only schematically shown in FIG. 12A and may be less complex than illustrated. As with the previously described embodiment, the dispensing apparatus 640 advantageously applies more volume of adhesive to the end portions 32, 36 of the elastic strands 28 than to the central portion 34, thereby significantly reducing adhesive use while maintaining similar high bond quality.

It will be understood that while the first and second dispensing modules 648, 650 and the first and second adhesive outlets 680, 682 are shown as directly parallel along the machine direction 46 in FIGS. 11 and 12A, another slightly modified embodiment of the dispensing apparatus 740 may include slightly offset elements along the machine direction 46. As shown in FIG. 12B, this dispensing apparatus 740 again includes first and second dispensing modules 748, 750 having first and second dispensing nozzles 742, 744 with first and second adhesive outlets 780, 782. The first dispensing module 748 is slightly offset forwards from the second dispensing module 750, which reduces or eliminates the entanglement of first and second filaments 756, 758 of adhesive during flight to the elastic strands 28. In all other respects, the dispensing apparatus 740 of FIG. 12B operates in an identical manner as the dispensing apparatus 640 of FIGS. 11 and 12A, and thus no further explanation is provided here.

Although the previous embodiments of the dispensing apparatus have included two separate dispensing modules and dispensing nozzles, it will be understood that the same method of applying more adhesive at the end portions 32, 34 of elastic strands 28 may be performed by a single dispensing module connected to an adjustable supply of adhesive 30 or multiple supplies of adhesive 30. In this regard, FIGS. 13-17 illustrate various embodiments of a dispensing apparatus 840, 940, 1040 that only include a single dispensing module and a single dispensing nozzle. These single module embodiments may include various types of dispensing nozzles, as described in further detail below.

With reference to FIG. 13, another embodiment of a dispensing apparatus 840 for applying varying volumes of adhesive along the length of elastic strands 28 in accordance with the invention is shown. Unlike previous embodiments, the dispensing apparatus 840 shown in FIG. 13 includes only a single dispensing module 848. The dispensing module 848 of this embodiment includes a contact dispensing nozzle 842 as described in U.S. patent application Ser. No. 61/474,129 to Saine. More particularly, and as described in further detail in U.S. patent application Ser. No. 61/474,129 to Saine, the dispensing nozzle 848 applies a quantity 856, 858 of adhesive, which is a quantity applied by contacting the elastic strand 28 with an extruded adhesive 30 and then blowing air onto the elastic strand 28 to spread the adhesive 30 around the elastic strand 28. Thus, in this embodiment, the dispensing nozzle 842 applies adhesive 30 individually onto each elastic strand 28. The quantity 856, 858 includes a first adhesive portion 856 that is thicker or includes more adhesive 30 than a second adhesive portion 858, as described in further detail below.

In order to apply these adhesive portions 856, 858 with different amounts of adhesive 30, the dispensing module 848 receives adhesive from two adhesive supplies 852, 854. Similar to the embodiments described above, the adhesive supplies 852, 854 may include separate individually adjustable pumps or a shared dual stream pump, depending on the particular application. The dispensing module 848 includes first and second valves 890, 892 configured to control whether a dispensing outlet 880 of the dispensing nozzle 842 receives adhesive from one, both, or neither of the adhesive supplies 852, 854. One alternative arrangement of the first and second valves 890, 892 is shown in FIG. 14, and another arrangement of the first and second valves 890a, 892a is shown in FIG. 15. It will be understood that the particular arrangement of the valves 890, 892 and how the module 848 actuates those valves 890, 892 may be modified in other manners without departing from the scope of the invention. For example, the module 848 may include a single source of actuation for both valves 890, 892 or independent sources of actuation, and the adhesive passages 894, 896 described below may not be angled relative to one another when a single source of actuation is used.

Turning to the arrangement shown in FIG. 14, the first valve 890 is positioned in a first angled passage 894 that receives adhesive 30 from the first adhesive supply 852. The second valve 892 is positioned in a second angled passage 896 receiving adhesive 30 from the second adhesive supply 854. Each of the first and second angled passages 894, 896 terminates in close proximity to the dispensing outlet 880, which is advantageous because this arrangement limits the passage space between the shutoff valves 890, 892 and the dispensing outlet 880 (to this end, flow of adhesive 30 is terminated proximate to the dispensing outlet 880 whenever one of the valves 890, 892 is closed). Thus, the amount of adhesive 30 that may drip or leak out of the dispensing nozzle 842 after the valves 890, 892 are closed is minimized. Additionally, the first and second valves 890, 892 are arranged in parallel within the dispensing module 848 such that each valve 890, 892 independently controls the on/off supply of adhesive 30 from the corresponding adhesive supplies 852, 854. This parallel arrangement of valves 890, 892 is similar to that arrangement which is described in U.S. Pat. No. 7,152,815 to Harris et al., the entire disclosure of which is hereby incorporated by reference herein. To this end, when both of the valves 890, 892 are open, a maximum flow of adhesive 30 is extruded through the dispensing outlet 880. When only one of the valves 890, 892 is open with the other closed, a lesser flow of adhesive 30 is extruded through the dispensing outlet 880. Thus, by controlling the operation of the valves 890, 892, the relative thickness of the coating formed by the quantity 856, 858 may be modified.

More particularly, the dispensing module 848 opens both valves 890, 892 to apply a thicker first adhesive portion 856 at the first and third portions 32, 36 of the elastic strands 28. The dispensing module 848 then closes one of the valves 890, 892 to apply a thinner second adhesive portion 858 at the second portion 34 of the elastic strands 28. When both valves 890, 892 are closed, substantially no adhesive 30 is extruded onto the elastic strands 28, such as for example at the free ends 38. Thus, as shown by the adhesive patterns shown in FIG. 13, the first and third portions 32, 36 are coated with first and third volumes of adhesive 30a, 30c that are larger than a second volume of adhesive 30b coating the second portions 34. As with the previously described embodiment, the dispensing apparatus 840 advantageously applies a higher volume of adhesive 30 to the end portions 32, 36 of the elastic strands 28 than to the central portions 34, thereby significantly reducing adhesive use while maintaining similar high bond quality.

In an alternative operation of the dispensing module 848 and valves 890, 892 shown in FIG. 14, the different flows or "volumes" of adhesive 30 are provided by selectively opening only one of the valves 890, 892 at a time. In such an arrangement, the separate individually adjustable pumps defining the first and second adhesive supplies 852, 854 are controlled to provide different (adjustable) amounts of flow of adhesive 30 into the first and second angled passages 894, 896. For example, the first adhesive supply 852 may be configured to deliver sufficient flow of adhesive 30 to produce a volume of 0.2 g/m on the elastic strands 28, while the second adhesive supply 854 may be configured to deliver sufficient flow of adhesive 30 to produce a volume of 0.1 g/m on the elastic strands 28. It will be understood that the exact volumes may be modified in other embodiments. As a result of these different amounts of flow, the dispensing module 848 achieves varying volumes by alternatively opening either the first valve 890 or the second valve 892. To this end, the dispensing module 848 opens the first valve 890 and closes the second valve 892 to apply a thicker first adhesive portion 856 at the first and third portions 32, 36 of the elastic strands. In between the first and third portions 32, 36, the dispensing module 848 closes the first valve 890 and opens the second valve 892 to apply a thinner second adhesive portion 858 at the second portion 34 of the elastic strands 28. When both valves 890, 892 are closed, substantially no adhesive 30 is extruded onto the elastic strands 28, such as for example at the free ends 38. In such an embodiment or operation, the valves 890, 892 are not configured to be opened at the same time, as the difference in volume output is provided by controlling the first and second adhesive supplies 852, 854 as described above.

It will be understood that the opening of the first valve 890 and/or the second valve 892 may be done in a continuous or intermittent manner during dispensing adhesive 30 onto the elastic strands 28. For example, the second portion 34 of the elastic strands 28 may be coated with the second adhesive portion 858 by keeping the first valve 890 closed and repeatedly opening and closing the second valve 892 to provide generally spaced-apart masses of adhesive 30 along the length of the second portion 34. Alternatively, the second portion 34 of the elastic strands 28 may be coated with the second adhesive portion 858 by keeping the second valve 892 continuously open while the first valve 890 is closed, which produces a generally uniform coating of adhesive 30 along the length of the second portion 34. It will be appreciated that the flow rate of adhesive 30 delivered by the individually adjustable pump defining the second adhesive supply 854 will be larger when the second valve 892 is to be opened intermittently than when the second valve 892 is to be opened continuously in order to provide the same level of adhesive coating on the second portion 34 of the elastic strands 28. Moreover, it will be understood that the application of adhesive 30 onto the first and third portions 32, 36 may be similarly adjusted by opening the first valve 890 intermittently or continuously in other embodiments.

Thus, just as in the previous exemplary operation, the first and third portions 32, 36 of the elastic strands 28 are coated with first and third volumes of adhesive 30a, 30c that are larger than a second volume of adhesive 30b coating the second portions 34 of the elastic strands 28. The application of a higher volume of adhesive 30 to the end portions 32, 36 of the elastic strands 28 than to the central portions 34 maintains high quality bonds capable of preventing creep at the opposing ends of the elastic strands 28 (defined by the end portions 32, 36) when adhesively secured to the substrate(s) 18, 26 to form the elasticized leg gather 20 on the disposable diaper 10. In other words, the integrity of the bonds formed between the elastic strands 28 and the substrate(s) 18, 26 is maintained by the first and third volume of adhesive 30a, 30c during normal wear conditions for the disposable diaper 10, and these bonds limit movement of the opposing ends of the elastic strands 28. Also, the reduced use of adhesive along the second portions 34 enables increased softness and force retraction capability for the disposable diaper 10 at least along these portions, compared to conventional designs. In this regard, the stiffness of the disposable diaper 10 is limited or reduced and the elastic strands 28 are allowed to retract from the stretched condition along the second portions 28.

Turning to FIG. 15, an alternative arrangement of the first and second valves 890a, 892a is shown. In this embodiment, the first valve 890a and the second valve 892a are arranged in series within the dispensing module 848. To this end, the first valve 890a is positioned in a first passage 894a that receives adhesive 30 from the first adhesive supply 852. The second valve 892a is positioned in a second passage 896a receiving adhesive 30 from the second adhesive supply 854. Contrary to the previous valve arrangement, the first passage 894a terminates into the second passage 896a just upstream of the second valve 892a. Thus, the second valve 892a operates to control on/off flow of both adhesive supplies 852, 854 into the dispensing outlet 880 simultaneously, while the first valve 890a only controls whether the flow past the second valve 892a originates from one or two adhesive supplies 852, 854.

In operation, opening both valves 890a, 892a again causes a maximum flow of adhesive 30 to be extruded through the dispensing outlet 880. When only the second valve 892a is open with the first valve 890a closed, a lesser flow of adhesive 30 is extruded through the dispensing outlet 880. When the second valve 892a is closed, substantially no adhesive 30 is extruded through the dispensing outlet 880 from either adhesive supply 852, 854. Consequently, the valve arrangement shown in FIG. 15 is operable to produce the same advantageous pattern of adhesive on the elastic strands 28 as described in regard to FIGS. 13 and 14.

With reference to FIG. 16, another embodiment of a dispensing apparatus 940 for applying varying volumes of adhesive along the length of elastic strands 28 in accordance with the invention is shown. As in the previous embodiment, the dispensing apparatus 940 shown in FIG. 16 includes only a single dispensing module 948. The dispensing module 948 of this embodiment includes a SureWrap® nozzle commercially available from Nordson Corporation of Westlake, Ohio. More particularly, the dispensing nozzle applies a quantity 956, 958 of adhesive formed by a filament impacted by a plurality of air jets to each elastic strand 28. The elastic strands 28 move faster than the quantity 956, 958 of adhesive, which causes the quantity 956, 958 to stretch out during application into discrete localized increased masses 74 on the strands 28 that are separated from one another by thinner (or broken) areas 76 of adhesive 30 running between adjacent masses 74. Thus, in this embodiment, the dispensing module 948 applies adhesive 30 individually onto each elastic strand 28. The quantity 956, 958 includes a first adhesive portion 956 that includes more adhesive 30 than a second adhesive portion 958, as indicated schematically by closer spaced masses 74 of adhesive 30 in the first adhesive portion 956.

In order to apply these adhesive portions 956, 958 with different amounts of adhesive 30, the dispensing module 948 receives adhesive from two adhesive supplies 952, 954. Similar to the embodiments described above, the adhesive supplies 952, 954 may include separate individually adjustable pumps or a shared dual stream pump, depending on the particular application. The dispensing module 948 includes first and second valves (not shown) configured to control whether a dispensing outlet (not shown) of the dispensing nozzle receives adhesive from one, both, or neither of the adhesive supplies 952, 954, as described above. Additionally, the dispensing module 948 also receives pressurized process air from two air supplies 953, 955. The pressurized air from these air supplies 953, 955 may be selectively controlled by similar valves as the adhesive 30, as well understood in the art. Accordingly, a higher amount of pressurized air may be used when a higher amount of adhesive 30 is being applied by the dispensing module 948. It will also be appreciated that the dispensing module 948 may receive a single adjustable pressurized air supply in other embodiments consistent with the scope of the invention. As with the previously described embodiments, the dispensing apparatus 940 advantageously applies more volume of adhesive to the end portions 32, 36 of the elastic strands 28 than to the central portion 34, thereby significantly reducing adhesive use while maintaining similar high bond quality.

With reference to FIG. 17, still another embodiment of a dispensing apparatus 1040 for applying varying volumes of adhesive along the length of elastic strands 28 in accordance with the invention is shown. As in the previous embodiment, the dispensing apparatus 1040 shown in FIG. 17 includes only a single dispensing module 1048. The dispensing module 1048 of this embodiment includes a Universal™ CF nozzle commercially available from Nordson Corporation of Westlake, Ohio. More particularly, the dispensing nozzle applies a quantity 1056, 1058 of adhesive formed by a swirled filament to all of the elastic strands 28 collectively. The quantity 1056, 1058 includes a first adhesive portion 1056 that includes more adhesive 30 than a second adhesive portion 1058, as indicated schematically by thicker and thinner swirl patterns shown in FIG. 17.

In order to apply these adhesive portions 1056, 1058 with different amounts of adhesive 30, the dispensing module 1048 receives adhesive from two adhesive supplies 1052, 1054. Similar to the embodiments described above, the adhesive supplies 1052, 1054 may include separate individually adjustable pumps or a shared dual stream pump, depending on the particular application. The dispensing module 1048 includes first and second valves (not shown) configured to control whether a dispensing outlet (not shown) of the dispensing nozzle receives adhesive from one, both, or neither of the adhesive supplies 1052, 1054, as described above. When both valves are open, the dispensing module 1048 applies the thicker first adhesive portion 1056 to the elastic strands 28. When only one of the valves is open, the dispensing module 1048 applies the thinner second adhesive portion 1058 to the elastic strands 28. As such, the dispensing apparatus 1040 advantageously applies more volume of adhesive to the end portions 32, 36 of the elastic strands 28 than to the central portion 34, thereby significantly reducing adhesive use while maintaining similar high bond quality.

While the present invention has been illustrated by the description of specific embodiments thereof, and while the embodiments have been described in considerable detail, it is not intended to restrict or in any way limit the scope of the appended claims to such detail. The various features discussed herein may be used alone or in any combination. Additional advantages and modifications will readily appear to those skilled in the art. The invention in its broader aspects is therefore not limited to the specific details, representative apparatus and methods and illustrative examples shown and described. Accordingly, departures may be made from such details without departing from the scope or spirit of the general inventive concept.

What is claimed is:

1. A dispensing apparatus for applying adhesive to at least one stretched elastic strand to be adhered to a substrate to form a personal disposable hygiene product, each elastic strand including first, second, and third portions along a length of the elastic strand, the dispensing apparatus comprising:
    a dispensing module;
    a single dispensing nozzle incorporated into the dispensing module, said single dispensing nozzle configured to dispense adhesive on the stretched elastic strand at each of the first, second, and third portions;
    a first valve positioned within said dispensing module and within said single dispensing nozzle, said first valve configured to be actuated between a first position and a second position, wherein in the first position of said first valve, a flow of adhesive from a first adhesive supply is allowed through said dispensing module to said single dispensing nozzle, and wherein in the second position of said first valve, said first valve stops a flow of the adhesive from the first adhesive supply through said dispensing module;
    a second valve positioned within said dispensing module and configured to be actuated between a first position and a second position, wherein in the first position of said second valve, a flow of adhesive from a second adhesive supply is allowed through said dispensing module to said single dispensing nozzle, and wherein in the second position of said second valve, said second valve stops a flow of adhesive from the second adhesive supply through said dispensing module;
    a strand guide adapted to guide the elastic strand relative to a dispensing outlet of said dispensing nozzle; and
    a controller operatively coupled to said first and second valves, said controller being configured to control said first valve to the first position and said second valve to the second position to apply a first volume of adhesive from the first adhesive supply to the first portion and a third volume of adhesive from the first adhesive supply to the third portion, said controller being further configured to control said first valve to the second position and said second valve to the first position to apply a second volume of adhesive from the second adhesive supply to the second portion, wherein the second volume of adhesive on the second portion is less than the first volume of adhesive on the first portion and less than the third volume of adhesive on the third portion, wherein the first and third portions of the elastic strand define opposing ends of the elastic strand when adhered to the substrate, and the second portion of the elastic strand defines a central portion of the elastic strand extending between the opposing ends when adhered to the substrate.

2. The dispensing apparatus of claim 1, wherein said first adhesive supply comprises a first individually adjustable pump for supplying an adjustable first flow rate of adhesive to said first valve of said dispensing nozzle, and said second adhesive supply comprises a second individually adjustable pump for supplying an adjustable second flow rate of adhesive to said second valve of said dispensing nozzle.

3. The dispensing apparatus of claim 1, further comprising:
    a dual stream pump producing a first outlet stream defining said first adhesive supply and a second outlet stream defining said second adhesive supply, the first and second outlet streams defining predetermined flows of adhesive delivered to said first and second valves of said dispensing nozzle.

4. The dispensing apparatus of claim 1, wherein said dispensing nozzle is a non-contact spray nozzle for applying a swirl pattern of adhesive onto the at least one elastic strand.

5. The dispensing apparatus of claim 1, wherein said dispensing nozzle is a contact nozzle for applying a continuous bead coating of adhesive onto the at least one elastic strand.

6. The dispensing apparatus of claim 1, wherein said controller is further configured to control each of said first and second valves to open continuously when in their respective first positions, such that the first, second and third volumes of adhesive define generally continuous adhesive coatings.

7. The dispensing apparatus of claim 1, wherein said controller is further configured to control each of said first and second valves to open intermittently when in their respective first positions, such that the first, second and third volumes of adhesive define a series of spaced apart or intermittent adhesive coatings.

8. The dispensing apparatus of claim 1, wherein said first and second valves are arranged generally in parallel to one another within said dispensing nozzle such that flows from said first and second valves combine downstream from each of said first and second valves and prior to discharge from a dispensing outlet of said dispensing nozzle.

9. The dispensing apparatus of claim 1, wherein said controller is further configured to control said first and second valves, such that the first and third portions of each elastic strand collectively define a first length and the second portion of each elastic strand defines a second length larger than the first length such that the second volume of adhesive is applied over a majority of the at least one elastic strand.

10. The dispensing apparatus of claim 9, wherein said controller is further configured to control said first and second valves, such that the first and third volumes of adhesive are sufficient to limit movement of the opposing ends of the at least one elastic strand relative to the substrate, and the second volume of adhesive is sufficiently low to allow the at least one elastic strand to retract from the stretched condition.

11. The dispensing apparatus of claim 1, wherein the single dispensing nozzle comprises a contact dispensing nozzle.

12. The dispensing apparatus of claim 1, wherein said second valve is positioned within said single dispensing nozzle.

13. The dispensing apparatus of claim 1, wherein said single dispensing nozzle is positioned between said dispensing module and said strand guide.

* * * * *